(12) United States Patent
Motoki

(10) Patent No.: US 6,555,372 B1
(45) Date of Patent: Apr. 29, 2003

(54) COMPOSITION FOR ENHANCING CELLULAR IMMUNOGENICITY COMPRISING ALPHA-GLYCOSYLCERAMIDES

(75) Inventor: Kazuhiro Motoki, Takasaki (JP)

(73) Assignee: Kirin Beer Kabushiki Kaisha, Tokyo-to (JP)

(*) Notice: Subject to any disclaimer, the term of this patent is extended or adjusted under 35 U.S.C. 154(b) by 0 days.

(21) Appl. No.: 09/509,087

(22) PCT Filed: Sep. 22, 1998

(86) PCT No.: PCT/JP98/04249

§ 371 (c)(1),
(2), (4) Date: Mar. 22, 2000

(87) PCT Pub. No.: WO99/15627

PCT Pub. Date: Apr. 1, 1999

(30) Foreign Application Priority Data

Sep. 22, 1997 (JP) .............................................. 9/257188

(51) Int. Cl.⁷ .......................... C12N 5/16; A61K 38/43; A61K 31/70
(52) U.S. Cl. .................... 435/326; 435/366; 435/372.1; 514/25; 424/93.6; 424/93.7; 424/573
(58) Field of Search ............... 424/93.6, 93.7, 424/573; 435/326, 366, 372.1; 514/25

(56) References Cited

U.S. PATENT DOCUMENTS 5,273,745 A * 12/1993 Schirrmacher ............... 424/89
5,767,092 A * 6/1998 Koezuka et al. ............... 514/25
5,858,776 A * 1/1999 Ostrand-Rosenberg ...... 435/325

FOREIGN PATENT DOCUMENTS

| EP | 0 694 558 | 1/1996 |
| EP | 0 957 161 | 11/1999 |
| EP | 0 988 860 | 3/2000 |

OTHER PUBLICATIONS

Yamaguchi et al., "Enhancing Effects of (2A,3S, 4R)–1–O–(αD–Galactopyranosyl)–2–(N–Hexacosanoylamino)–1,3,4–Octadecanetriol (KRN700) On Antigen–Presenting Function Of AntigenPresenting Cells And Antimetastatic Activity of KRN7000–Pretreated Antigen–Presenting Cells", *Oncology Research*, vol. 8(10/11):399–407, (1996).

Motoki et al., "Effects Of α–Galactosylceramides On Bone Marrow Cells in Vitro and Hematopoiesis in Vivo", *Biol. Pharm. Bull.*, vol. 19(7):952–955, (1996).

* cited by examiner

*Primary Examiner*—Kathleen K. Fonda
*Assistant Examiner*—Leigh C. Maier
(74) *Attorney, Agent, or Firm*—Foley & Lardner

(57) ABSTRACT

A composition for enhancing immunogenicity of tumor cells or pathogen-infected cells comprising a compound having an α-glycosylceramide structure or a salt or solvate thereof is provided. Tumor cells of which immunogenicity is enhanced by the compound having an α-glycosylceramide structure are useful for tumor therapy (cancer vaccine therapy).

7 Claims, 8 Drawing Sheets

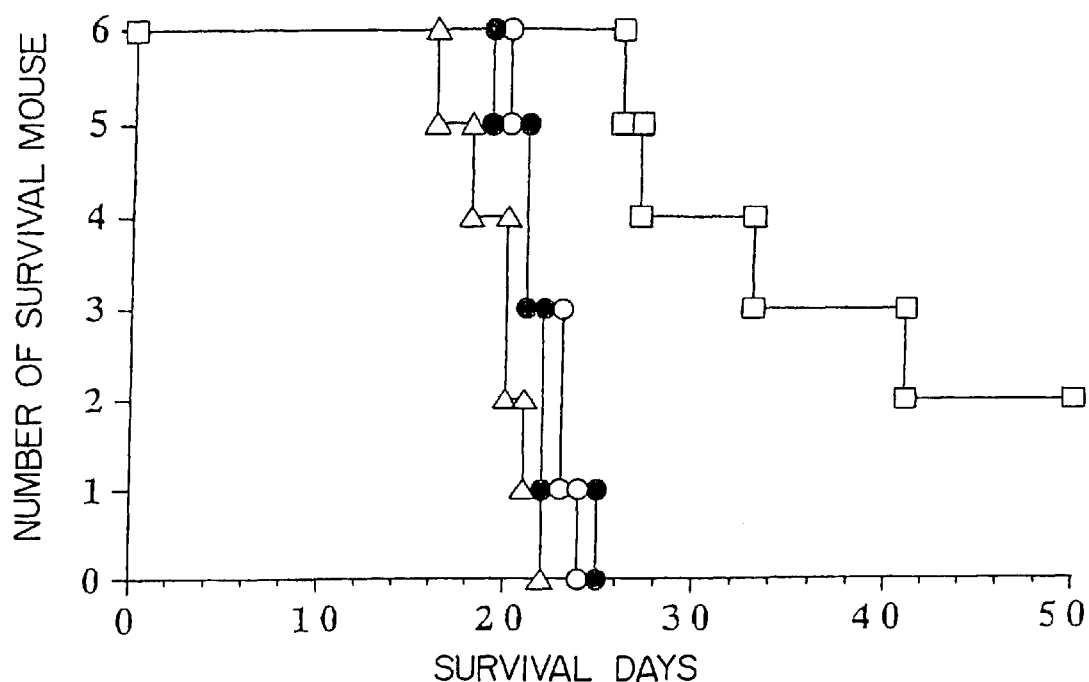
F I G. 2
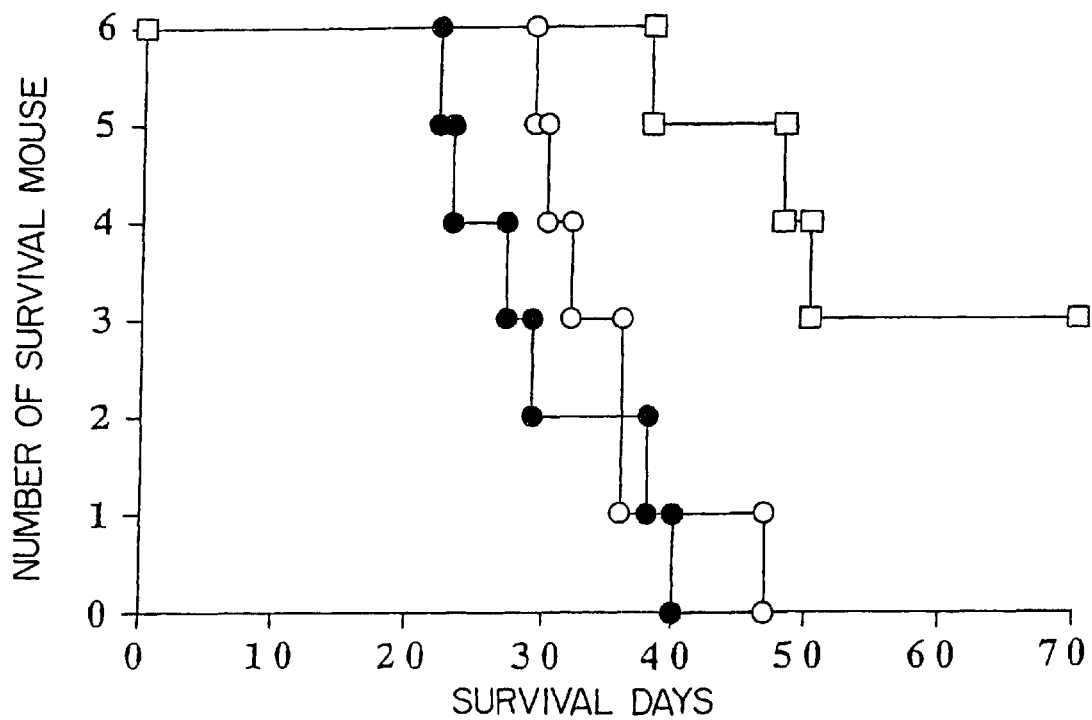
F I G. 3

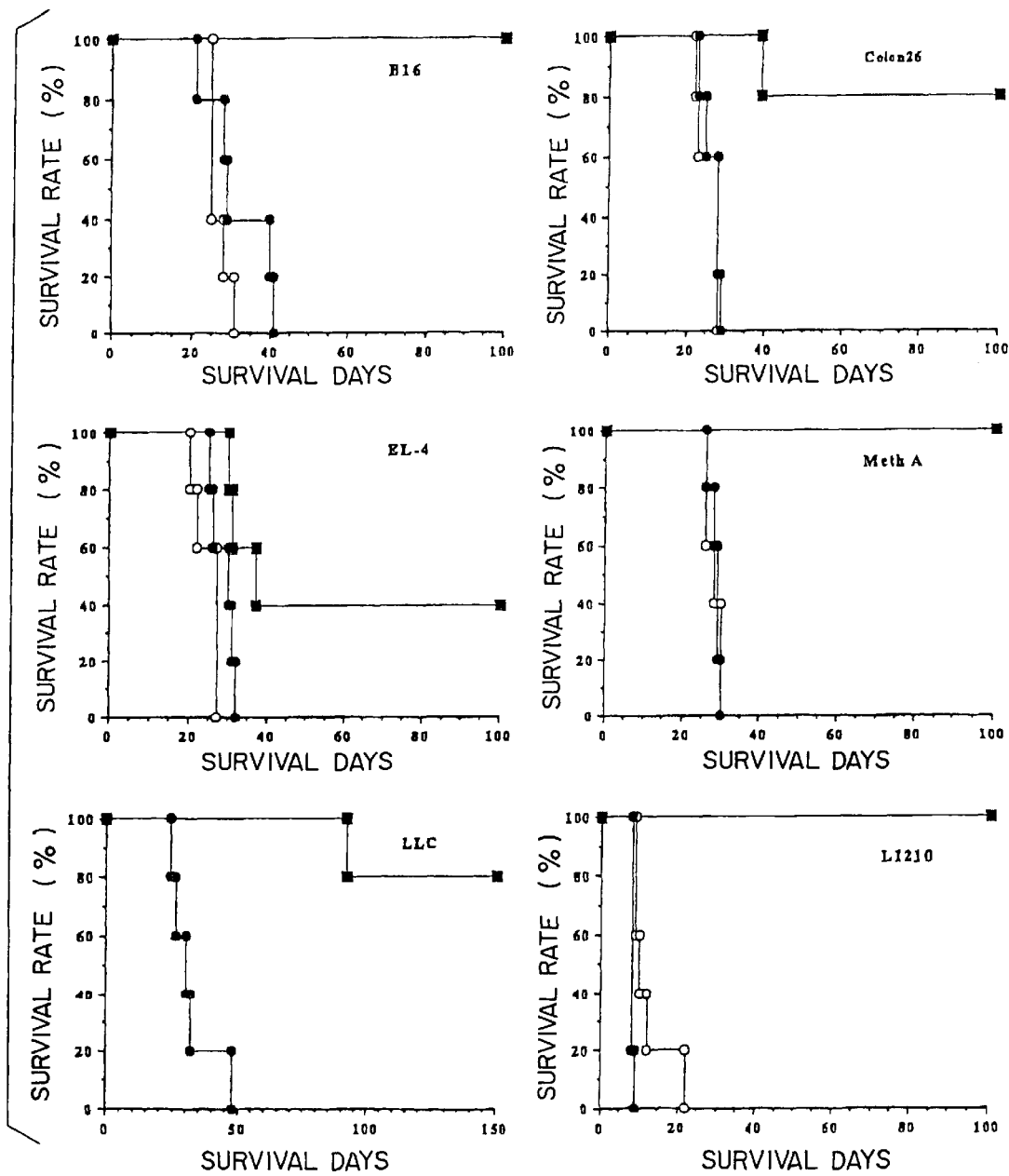
F I G. 4

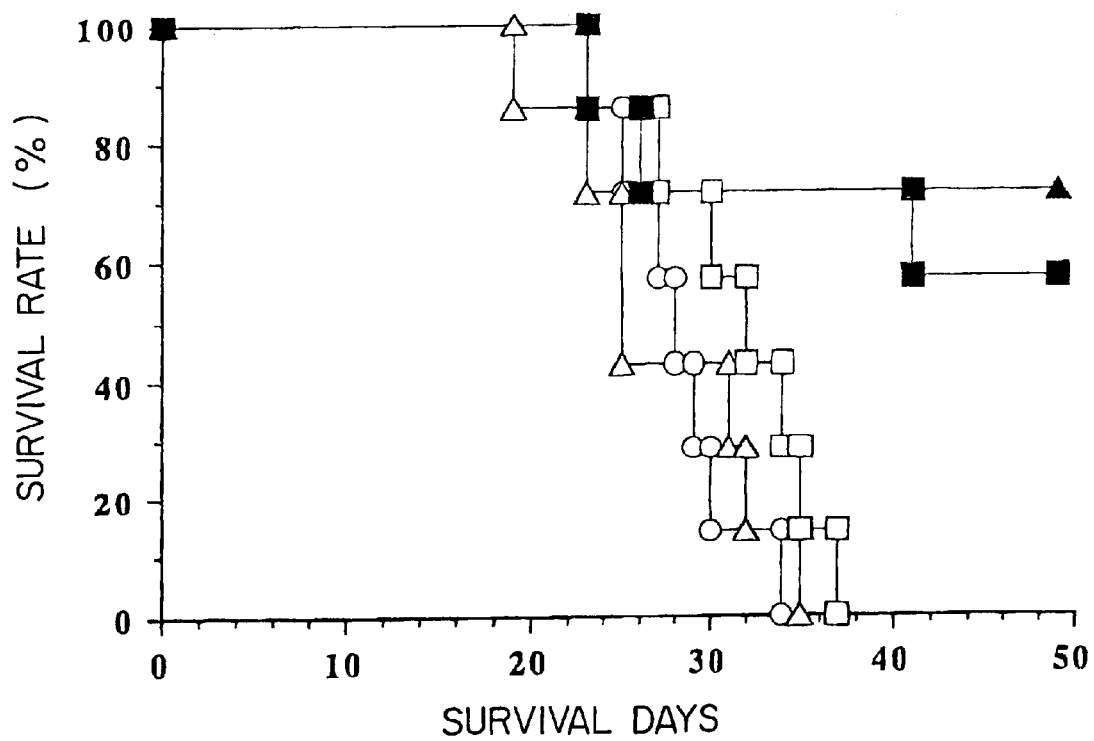
F I G. 5

KRN7000

AGL-517

AGL-563

AGL-571

AGL-577

COMPOSITION FOR ENHANCING CELLULAR IMMUNOGENICITY COMPRISING ALPHA-GLYCOSYLCERAMIDES

This application is the national stage entry of PCT/JP98/04249, filed Sep. 22, 1998.

BACKGROUND OF THE INVENTION

1. Field of the Invention

The present invention relates to a method of enhancing immunogenicity of tumor cells and pathogen-infected cells using a compound having an α-glycosylceramide structure, and more particularly to tumor therapy using tumor cells of which immunogenicity is enhanced.

2. Background Art

In order to treat tumors including melanoma (Mitchell, M. S. et al., J. Clin. Oncol., 8, 409 (1990)), kidney cancer (Neidart, J. A. et al., Cancer, 46, 1128 (1980)), ovarian cancer (Freedman, R. S. et al., Gynecol. Oncol., 29, 337 (1988)), and colon cancer (Hoover, H. C., Cancer, 55, 1236 (1985)), attempts were made to induce tumor-specific immunity in the cancer-bearing hosts by immunizing patients with autologous or allogeneic tumor cells previously inactivated by chemotherapeutic agents or radiation. However, immunogenicity of tumor cells is relatively low different from that of foreign substances such as bacteria because these are originally transformed from host cells. Thus, effectiveness was not as anticipated and only a minor effect was observed in cancers such as melanoma or kidney cancer of which immunogenicity is relatively high (Mullen, C. A. et al., in Cancer Chemotherapy and Biological Response Modifiers, eds. Pinedo, H. M. et al., Elsevier Science B. V.), pp 285–294 (1996)).

Recent developments in molecular biology and genetic engineering made it possible to introduce genes, and it was attempted to apply genetically modified tumor cells expressing cancer-related antigen for cancer therapy. For example, tumor antigen genes were transduced into autologous tumor cells, or otherwise non-self tumor cells if it is difficult to obtain autologous tumor, and obtained tumor cells of which immunogenicity was increased over the original tumor cells were used in tumor therapy. However, at this time, since only a small number of antigens are identified as tumor-related antigens, such attempts are carried out only for limited kinds of cancers (Conry, R. M. et al., Cancer Res., 54, 1164 (1994)). Furthermore, it has been revealed that therapeutic efficacy cannot be attained as anticipated by simply enhancing antigenicity of tumor cells because the immunity of cancer-bearing hosts is often markedly impaired by factors produced by tumor cells, or the like, so that it is rather important to restore the immunity of the cancer-bearing hosts. Consequently, recent studies are mainly focused on attempts to restore the impaired host immunity by immunizing them with cells to which cytokine genes, major histocompatible antigen genes, costimulatory molecules or the like are introduced in order to improve the therapeutic effect. Examples of the tumor cells used in reported studies include those to which cytokine genes such as IL-2 (Connor, J. et al., J. Exp. Med., 177, 1127 (1993)), IL-4 (Golumbek, P. T. et al., Science, 254, 713 (1991)), IL-6 (Porgador, A. et al., Cancer Res., 52, 3679 (1992)), IFN-g (Belldegrun, A. et al., J. Natl. Cancer Inst., 85, 207 (1993)), GM-CSF (Dranoff, G. et al., Proc. Natl. Acad. Sci. USA, 90, 3539 (1993)), IL-12 (Tahara, H. et al., Gene Therapy, 2, 96 (1995)) were introduced, and those to which MHC class II and B7-1 genes (Travis, J. et al., Science, 259, 310 (1993); Basker, S. et al., J. Exp. Med., 181, 619 (1995)) were introduced.

Thus, tumor therapy using tumor cells modified by gene transfer is tested for clinical application all over the world (Roth, J. A. et al., J. Natl. Cancer Inst., 89, 21 (1997). However, gene manipulation for this procedure is complicated (Pardoll, D. M., Immunol. Today, 14, 310 (1993)). Furthermore, vectors which introduce genes efficiently to obtain sufficient therapeutic efficacy have not been developed. Thus, there is a need for further improvement in the tumor therapy described above (Mullen, C. A. et al., in Cancer Chemotherapy and Biological Response Modifiers, eds. Pinedo, H. M. et al. (Elsevier Science B. V.), pp 285–294 (1996).

β-Glycosylceramides, in which various sugars bind to ceramides via a β-bond, can be found in the body (Svennerholm, L. et al., Biochem. Biophys. Acta, 280, 626 (1972); Karlsson, K. et al., Biochem. Biophys. Acta, 316, 317 (1973)). On the other hand, it is known that α-glycosylceramides have marked immunostimulatory activity and antitumor activity (Morita, M. et al., J. Med. Chem., 38, 2176 (1995)). Such activities by α-glycosylceramides are known to be much stronger than those by β-glycosylceramides (Motoki, K. et al., Biol. Pharm. Bull., 18, 1487 (1995)). Furthermore, it is known that compounds having an α-glycosylceramide structure can augment antigen-presenting function of antigen presenting cells, and tumor therapy using the antigen-presenting cells stimulated by compounds having an α-glycosylceramide structure is very effective. It is also known that administration of compounds having an α-glycosylceramide structure protect the body from radiation (Motoki, K. et al., Bioorg. Med. Chem. Lett., 5, 2413 (1995)), and increases the number of platelets and leukocytes (Motoki, K. et al., Biol. Pharm. Bull., 19, 952 (1996)).

However, as far as the present inventors know, there is no report that tumor cells treated with α-glycosylceramides are useful in tumor therapy and that α-glycosylceramides enhance immunogenicity of tumor cells.

SUMMARY OF THE INVENTION

The present inventors have now found that tumor cells which were cultured in vitro in a medium containing a compound having an α-glycosylceramide structure showed high immunogenicity, that a marked antitumor effect was observed by administrating the cells above or the cells modified by radiation to cancer-bearing animals, and that the cells were highly safe in tumor therapy because their tumorigenicity is lost. The present invention is based on these findings.

An objective of the present invention is to provide a composition for enhancing immunogenicity of tumor cells, by which the tumor cells effective for tumor therapy can be readily prepared; a composition for enhancing immunogenicity of pathogen-infected cells, by which pathogen-infected cells effective for the treatment of infectious diseases or the like can be readily prepared; a method for enhancing immunogenicity of cells; cells of which immunogenicity is enhanced by an α-glycosylceramide; a pharmaceutical composition comprising the cells above for the treatment of diseases, particularly tumors, associated with the cells; use of the cells for the manufacture of the pharmaceutical composition, and a method for the treatment of diseases, particularly tumors, associated with the cells.

A composition for enhancing immunogenicity of tumor cells or pathogen-infected cells according to the present invention comprises a compound of formula (I):

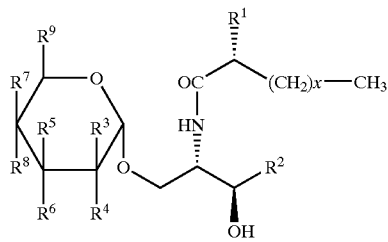
(I)

wherein $R^1$ represents H or OH,

X represents an integer between 7 and 27, $R^2$ represents a substituent selected from the group consisting of the following (a) to (e) (wherein Y represents an integer between 5 and 17):
  (a) —$CH_2(CH_2)_YCH_3$
  (b) —$CH(OH)(CH_2)_YCH_3$
  (c) —$CH(OH)(CH_2)_YCH(CH_3)_2$
  (d) —$CH=CH(CH_2)_YCH_3$
  (e) —$CH(OH)(CH_2)_YCH(CH_3)CH_2CH_3$, and $R^3$ to $R^9$ represent substituents as defined in any one of the following i) and ii):
  i) when $R^3$, $R^6$ and $R^8$ represent H,
    $R^4$ represents H, OH, $NH_2$, $NHCOCH_3$, or a substituent selected from the group consisting of the following groups (A) to (D):

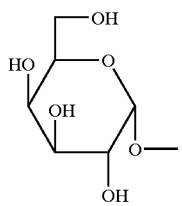
(A)

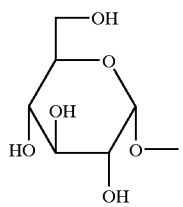
(B)

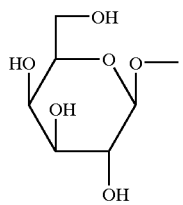
(C)

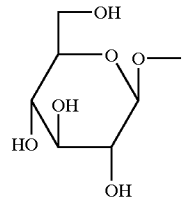
(D)

$R^5$ represents OH or a substituent selected from the group consisting of the following groups (E) and (F):

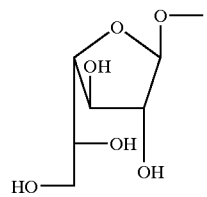
(E)

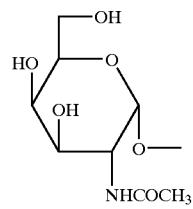
(F)

$R^7$ represents OH or a substituent selected from the group consisting of the following groups (A) to (D):

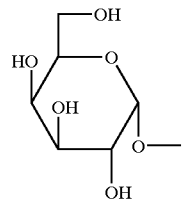
(A)

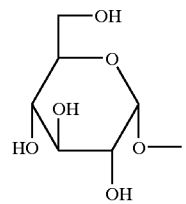
(B)

-continued

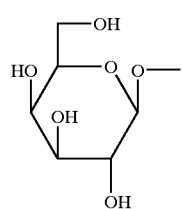
(C)

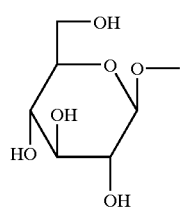
(D)

R⁹ represents H, CH₃, CH₂OH or a substituent selected from the group consisting of the following groups (A') to (D'):

(A')

(B')

(C')

(D')

ii) when R³, R⁶ and R⁷ represent H,

R⁴ represents H, OH, NH₂, NHCOCH₃, or a substituent selected from the group consisting of the following groups (A) to (D):

(A)

(B)

(C)

(D)

R⁵ represents OH or a substituent selected from the group consisting of groups (E) and (F):

(E)

(F)

R⁸ represents OH or a substituent selected from the group consisting of the following groups (A) to (D):

(A)

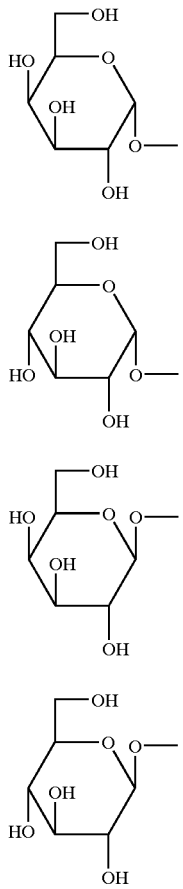

$R^9$ represents H, CH$_3$, CH$_2$OH or a substituent selected from the group consisting of the following groups (A') to (D'):

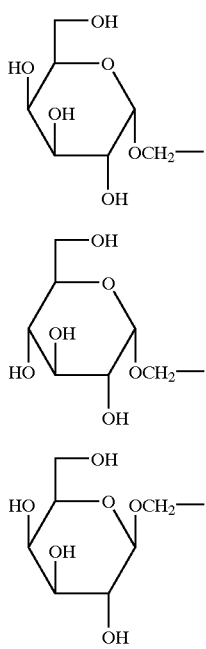

(D')

or a salt or solvate thereof.

BRIEF DESCRIPTION OF THE DRAWINGS

FIG. 2 shows the antitumor effect of α-glycosylceramide-treated tumor cells in EL-4 liver metastasis model mice. ○: Control, ●: EL-4/V, □: EL-4/KRN, Δ: EL-4/583.

FIG. 3 shows the antitumor effect of α-glycosylceramide-treated tumor cells in B16 melanoma lung metastasis model mice. ○: Control, ●: B16/V, □: B16/KRN.

FIG. 4 shows the effect of α-glycosylceramides on tumorigenicity of severl murine tumors. ○: Untreated tumor cells, ●: tumor cells treated with a vehicle, ■: tumor cells treated with KRN 7000.

FIG. 5 shows the effect of α-glycosylceramide-treated irradiated or non-irradiated tumor cells in B16 melanoma lung metastasis model mice. ○: Control, Δ: non-radiated B16/V, □: radiated B16/V, ▲: non-radiated B16/K, ■: radiated B16/K.

DETAILED DESCRIPTION OF THE INVENTION

Compounds of Formula (I)

Figure 1:
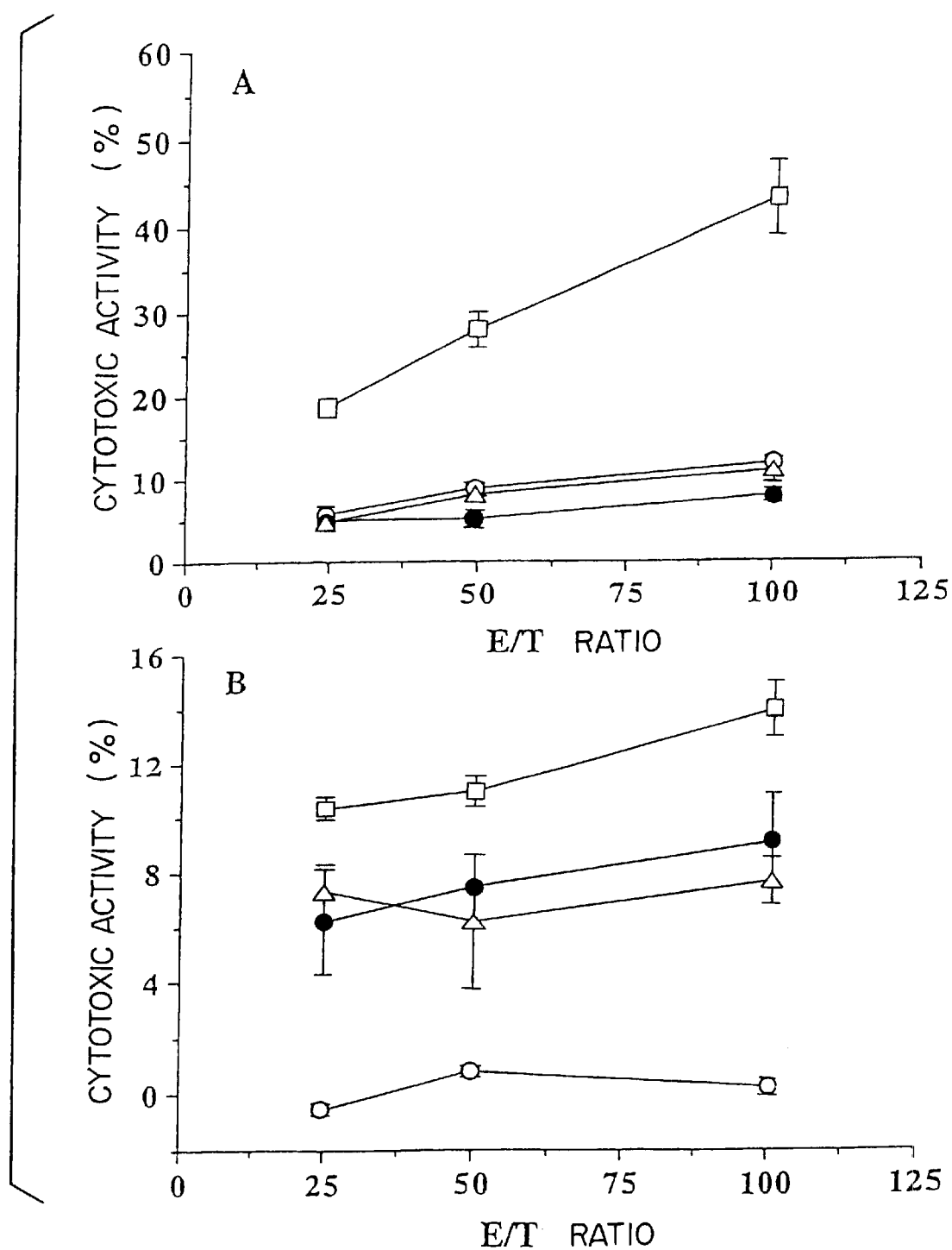
FIG. 1 shows the effect of α-glycosylceramides on immunogenicity of tumor cells. Immunogenicity is evaluated with cytotoxic activity of mouse spleen cells. ○: Control, ●: EL-4/V, □: EL-4/KRN, Δ: EL-4/583.

In the compounds of formula (I), X in the ceramide moiety preferably represents an integer between 11 and 25.

Y in $R^2$ preferably represents an integer between 9 and 17, more preferably between 11 and 15.

Preferable combinations for X and $R^2$ in the ceramide moiety of formula (I) are compounds in which X is an integer between 21 and 25 and $R^2$ is substituent (b) (wherein Y is an integer between 11 and 15).

Preferable combinations for $R^3$ to $R^9$ in the sugar moiety of formula (I) are compounds in which $R^3$ and $R^6$ are H, $R^4$ is OH or any substituent of groups (A) to (D), $R^5$ is OH or any substituent of group (E) or (F), $R^7$ and $R^8$ are each H or OH ($R^7$ and $R^8$ does not represent the same substituent), and $R^9$ is $CH_2OH$, $CH_3$, H or any substituent of groups (A') to (D').

More preferable combinations include compounds in which $R^3$ and $R^6$ are H, $R^4$ and $R^5$ are OH, $R^7$ and $R^8$ are each H or OH ($R^7$ and $R^8$ does not represent the same substituent), and $R^9$ is $CH_2OH$ or any substituent of groups (A') to (D'), and compounds in which $R^3$, $R^6$ and $R^8$ are H, $R^4$, $R^5$ and $R^7$ are OH, and $R^9$ is $CH_2OH$.

Preferable examples of compounds of formula (I) include compounds in which

X is an integer between 21 and 25,
$R^2$ is substituent (b) (wherein Y is an integer between 11 and 15),
$R^3$ and $R^6$ are H,
$R^4$ is OH or a group selected from the group consisting of groups (A) to (D),
$R^5$ is OH or a group selected from the group consisting of groups (E) and (F),
$R^7$ and $R^8$ are each H or OH ($R^7$ and $R^8$ does not represent the same substituent), and
$R^9$ is $CH_2OH$ or a group selected from the group consisting of groups (A') to (D');

compounds in which

X is an integer between 21 and 25,
$R^2$ is substituent (b) (wherein Y is an integer between 11 and 15),
$R^3$ and $R^6$ are H,
$R^4$ and $R^5$ are OH,
$R^7$ and $R^8$ are each H or OH ($R^7$ and $R^8$ does not represent the same substituent), and
$R^9$ is $CH_2OH$ or a group selected from the group consisting of groups (A') to (D'); and compounds in which X is an integer between 21 and 25,
$R^2$ is substituent (b) (wherein Y is an integer between 11 and 15),
$R^3$, $R^6$ and $R^8$ are H,
$R^4$, $R^5$ and $R^7$ are OH, and
$R^9$ is $CH_2OH$.

Preferable compounds as effective components of therapeutic agents according to the present invention include (2S,3S,4R)-1-(α-D-galactopyranosyloxy)-2-hexacosanoylamino-3,4-octadecanediol (KRN 7000).

The compounds of formula (I) may be in the form of pharmaceutically acceptable nontoxic salts thereof. Salts of formula (I) include acid added salts, such as salts with inorganic acids (e.g., hydrochloric acid, sulfuric acid, nitric acid and phosphoric acid) or with organic acids (e.g., acetic acid, propionic acid, maleic acid, oleic acid, palmitic acid, citric acid, succinic acid, tartaric acid, fumaric acid, glutamic acid, pantothenic acid, laurylsulfonic acid, methanesulfonic acid and phthalic acid).

The compounds of formula (I) may be in the form of solvates thereof (e.g., hydrates).

The compounds of formula (I) can be produced by any purposive method to synthesize α-glycosylceramides.

First, a ceramide moiety is synthesized using D-lyxose as a starting material, then a sugar is introduced into this ceramide to prepare compounds of formula (I). A general method to synthesize such α-glycosylceramides can be found, for example, in WO93/5055, WO94/2168, WO/9020 and WO94/24142.

The compounds of formula (I) can also be isolated from natural products (e.g., biological organisms) and purified by column chromatography or the like.

Compositions for Enhancing Cellular Immunogenicity

Compounds of formula (I) were shown to be useful in enhancing cellular immunogenicity (Pharmacological Test Examples 1 to 5). The term "immunogenicity" used herein refers to an activity for cells to elicit an immune response in the body, and an activity to be recognized by the immune system induced thereof.

Compositions for enhancing immunogenicity according to the present invention are used by contacting in vitro cells of which immunogenicity is to be enhanced by the compositions. For example, a composition for enhancing immunogenicity according to the present invention was added to culture medium at a final concentration of the compound of formula (I) of 0.1 to 10,000 ng/ml (preferably 1 to 1,000 ng/ml), and the cells were cultured in the medium for 30 minutes to 4 days (preferably 3 hours to 2 days) to enhance immunogenicity of the cells. The conditions for culturing the cells and the culture medium to be used can be selected according to the conventional techniques.

The compositions for enhancing cellular immunogenicity according to the present invention in the form of a solution, suspension or emulsion can be added to a cell culture.

The compositions in these various forms can contain pharmaceutically acceptable carriers or additives such as diluents, more specifically, solvents (e.g., water and physiological saline), solubilizing agents (e.g., ethanol and polysolvates), isotonic agents, preservatives, antioxidants, excipients (e.g., lactose, starch, crystalline cellulose, mannitol, maltose, calcium hydrogenphosphate, soft silicic acid anhydride and calcium carbonate), binding agents (e.g., starch, polyvinyl pyrrolidone, hydroxypropylcellulose, ethylcellulose, carboxymethylcellulose and gum arabic), stabilizing agents (e.g., lactose, mannitol, maltose, polysolvates, macrogols, and polyoxyethylene hydrogenated castor oil), disintegrating agents (e.g., starch and carboxymethylcellulose calcium), and lubricating agents (e.g., magnesium stearate, talc and hydrogenated oil).

If necessary, glycerol, dimethyacetamide, 70% sodium lactate, surfactants and alkaline substances (e.g., ethylenediamine, ethanol amine, sodium carbonate, arginine, meglumine and trisaminomethane) can also be added.

When tumor cells contacted with the compound of formula (I) is immunized into mice, immunity to the tumor cells (cytotoxic activity) is induced. Surprisingly, immunity to other tumor cells than the immunized tumor itself is induced (see Pharmacological Test Example 1).

Cells of which immunogenicity is to be enhanced can be tumor cells or pathogen-infected cells. These cells can be isolated from patients having tumors or patients infected with pathogens, or artificially produced in vitro.

Examples of tumor cells of which immunogenicity is to be enhanced include virtually all cancer cells including melanoma, kidney cancer, uterine cancer, pancreatic cancer, cerebral tumor, glioblastoma, colon cancer, lung cancer, hepatoma, lymphoma, leukemia, and fibrosarcoma. In particular, melanoma and kidney cancer cells are preferable.

Examples of pathogen-infected cells include those infected with viruses. The term "pathogen" herein includes pathogenic agents such as Chlamydiae, Rickettsiae, *Listeria monocytogenes*, Leishmaniae, Trypanosomas and prion proteins.

The present invention provides a method of enhancing cellular immunogenicity, which comprises the step of contacting cells with the compound of formula (I), or a salt or solvate thereof. The contact of the cells with the compound of formula (I) can be carried out in the same manner as described above.

Immunogenicity-enhanced Cells

The immunogenicity-enhanced cells according to the present invention can be obtained by contacting in vitro the compound of formula (I) or a salt or solvate thereof with cells of which immunogenicity is to be enhanced. The immunogenicity-enhanced cells can be prepared under the conditions as described above.

Administration of the immunogenicity-enhanced cells to mammals as an antigen induces a strong immunity to the cells, and a disease associated with the cells can be treated.

Accordingly, the present invention provides a therapeutic agent for the treatment of diseases, comprising immunogenicity-enhanced cells which can be obtained by contacting cells associated with the diseases with the compound of formula (I) or a salt or solvate thereof. The term "therapy" as used herein also means "prevention".

The present invention also provides a method for the treatment of diseases, comprising the step of administering immunogenicity-enhanced cells which can be obtained by contacting cells associated with the diseases with the compound of formula (I) or a salt or solvate thereof.

Tumors can be treated using immunogenicity-enhanced tumor cells as an active ingredient. Infectious diseases can be treated using pathogen-infected cells of which immunogenicity is enhanced as an active ingredient.

A strong immunity to tumor cells is induced by immunizing the body with tumor cells, of which immunogenicity is enhanced by the compound of formula (I). As a result, tumors are attacked by the immune system, leading to tumor regression or eradication. The tumor cells according to the present invention induced strong immunity not only to tumors such as melanoma of which immunogenicity is known to be high, but also to tumors such as T lymphoma (see Pharmacological Test Examples 2 and 3).

Thus, the present invention provides a pharmaceutical composition for the treatment of tumors, comprising immunogenicity-enhanced tumor cells obtained by contacting tumor cells with the compound of formula (I) or a salt or solvate thereof, in vitro.

The present invention also provides a method for the treatment of tumors, comprising the administration of the immunogenicity-enhanced tumor cells.

The term "tumor" as used herein means cancers including melanoma, kidney cancer, uterine cancer, pancreatic cancer, cerebral tumor, glioblastoma, colon cancer, lung cancer, hepatoma, lymphoma, leukemia, fibrosarcoma, and the like.

The term "pharmaceutical composition for the treatment of tumors" as used herein includes agents for cancer treatment such as cancer vaccines or cancer cell vaccines.

In the present invention, the immunogenicity-enhanced cells can be administered through any purposive routes, for example, intraperitoneal or subcutaneous administration, intravenous or intra-arterial administration and local administration by injection. Furthermore, when administered to humans, intravenous or intra-arterial administration, local administration by injection, intraperitoneal or intrathoracic administration, subcutaneous administration, or intramuscular administration can be used. Intravenous administration is most preferable.

In the present invention, the immunogenicity-enhanced cells can be administered in dosage forms such as injectable agents, suspensions and emulsions based on conventional methods. If necessary, in order to further enhance the immunogenicity of cells, the cells can be suspended in adjuvants such as Freund's complete adjuvant, or the cells can be administered with substances having an adjuvant activity, such as BCG. Pharmaceutical compositions for the treatment of tumors according to the present invention can contain the abovementioned pharmaceutically acceptable carriers and auxiliaries.

An active ingredient of the pharmaceutical compositions of the present invention can be administered continuously or intermittently depending on the specific conditions. Actual doses can be determined depending on a variety of factors such as the administration routes, the conditions of the patients such as age, body weight, sex, and sensitivity, period of administration, and other drugs taken in combination. A daily dose required to exert the activity of immunogenicity-enhanced tumor cells for an adult human, for example for intravenous administration, is generally $1 \times 10^5$ to $1 \times 10^9$ cells/kg body weight, preferably $1 \times 10^6$ to $5 \times 10^8$ cells/kg body weight. The immunogenicity-enhanced cells are preferably formulated into injectable agents, which can be administered without further processing at a previously adjusted specified concentration, or diluted to a specified concentration with injection-grade physiological saline or the like, immediately before administration to patients.

The immunogenicity-enhanced cells according to the present invention can be killed, or their proliferative ability can be abolished by radiation or treating with a cytotoxic agent prior to administration to patients.

EXAMPLES

The present invention is further illustrated by the following examples that are not intended as a limitation of the invention.

Synthesis, Isolation and Purification of Compounds

Example 1

Synthesis of (2S,3S,4R)-1-(α-D-galactopyranosyloxy)-2-hexacosanoylamino-3,4-octadecanediol (KRN 7000)

Figure 6:
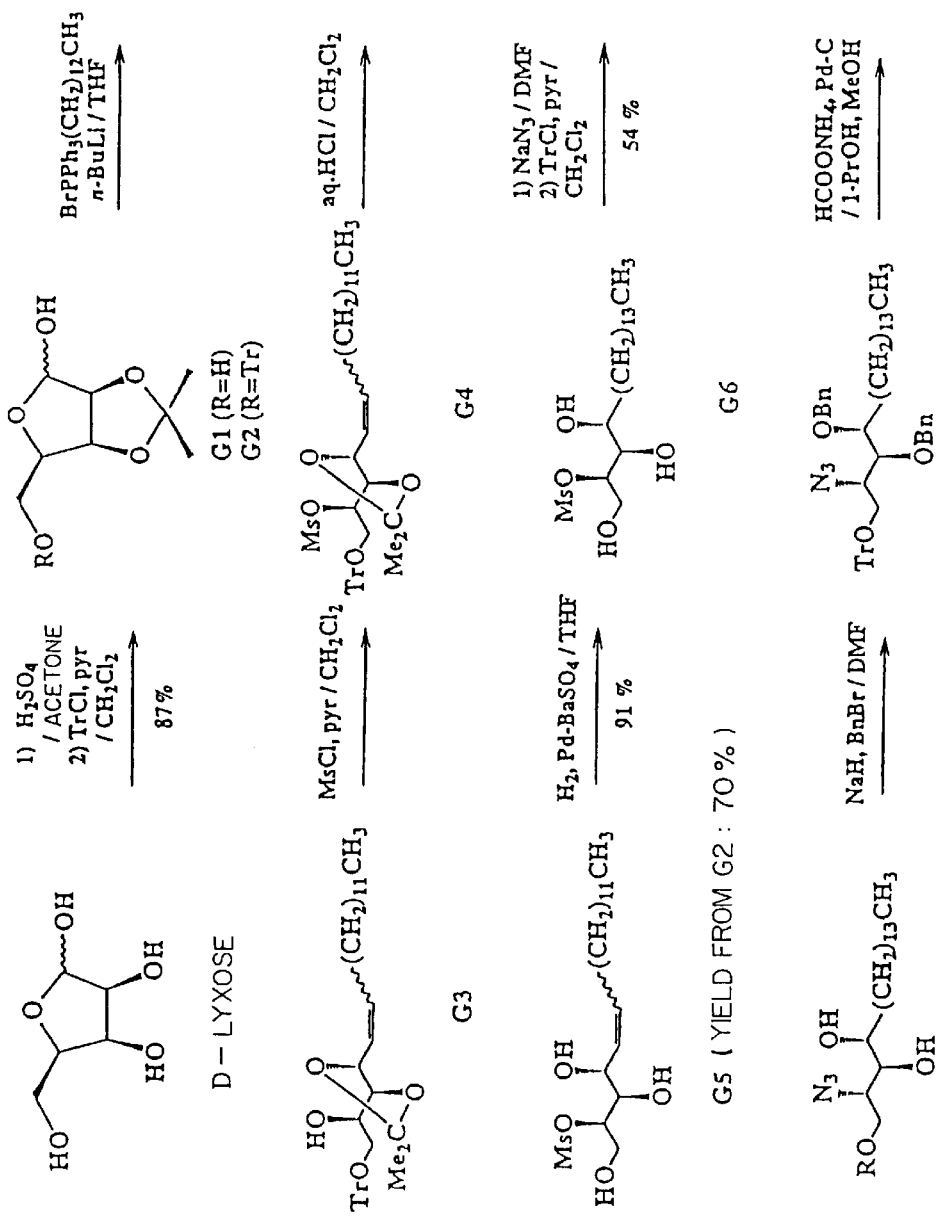
FIG. 6 shows the outline of reactions for the synthesis of KRN 7000, the representative α-glycosylceramide compound used in the present invention. In the drawing, pyr represents pyridine, BrPPh$_3$ (CH$_2$)$_{12}$CH$_3$ represents tridecanetriphenylphosphonium bromide, n-BuLi represents n-butyl lithium, MsCl represents methanesulfonyl chloride, BnBr represents benzyl bromide, and 1-PrOH represents propyl alcohol.
Figure 7:
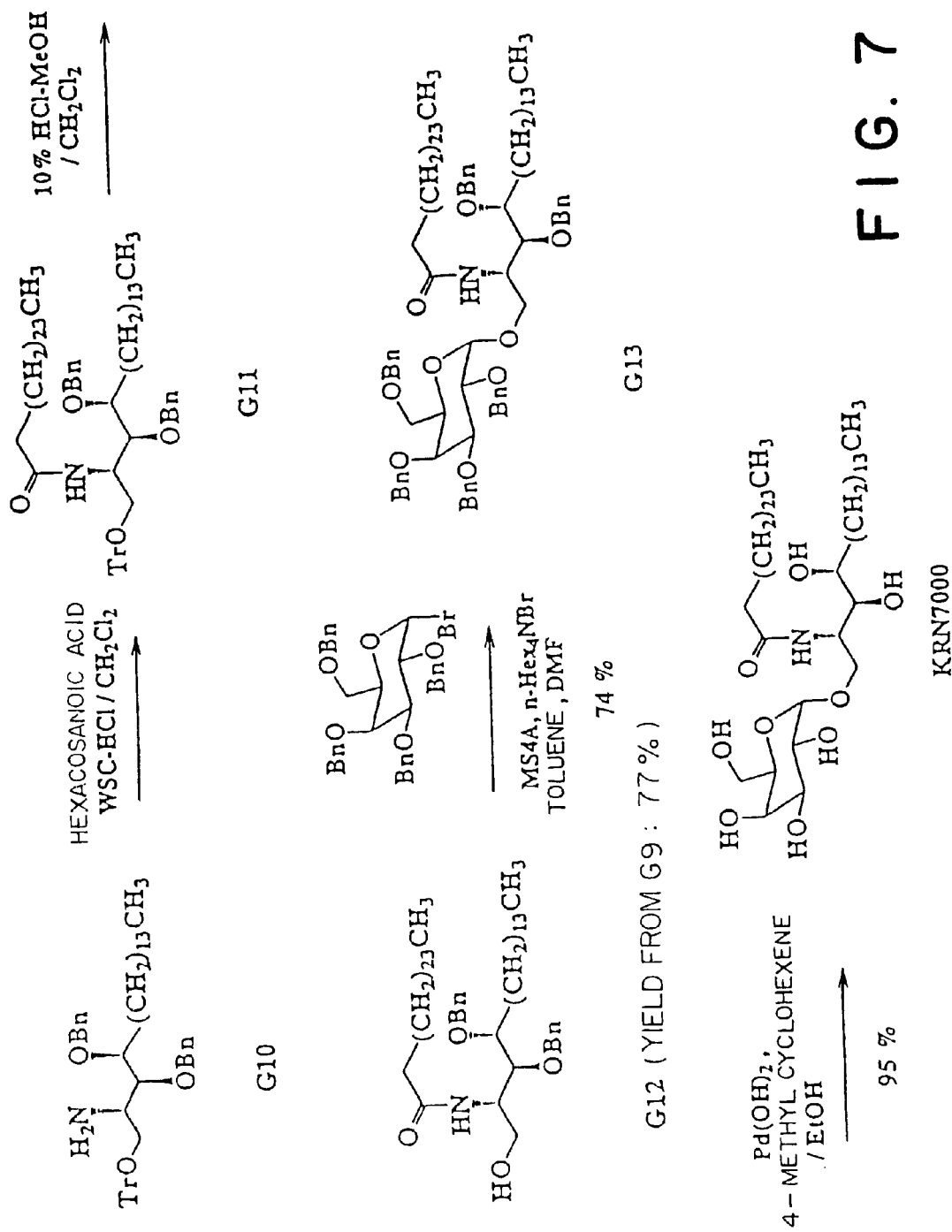
FIG. 7 is the continuation of the reactions for the synthesis as shown in FIG. 6. WSC-HCl represents 1-ethyl-3-(3'-dimethylaminopropyl)-carbodiimide hydrochloride, MS4A represents molecular sieves 4A, and Hex4NBr represents tetrahexylammonium bromide.
Figure 8:
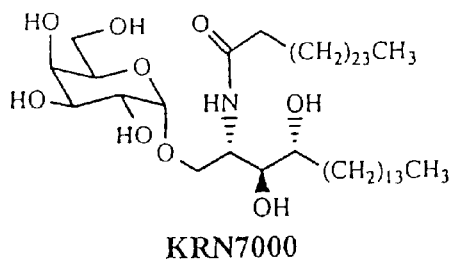
FIG. 8 shows chemical formulas of the compounds in Examples 1 to 3.
Figure 8:
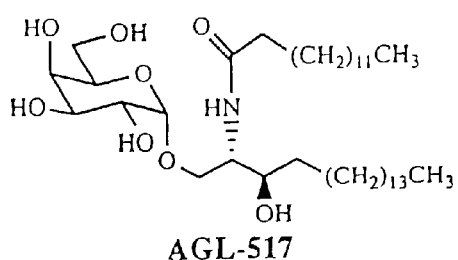
Figure 8:
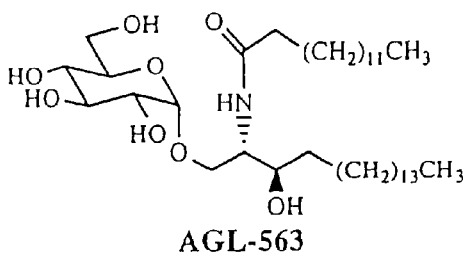
Figure 8:
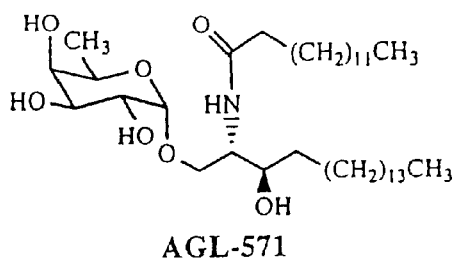
Figure 8:
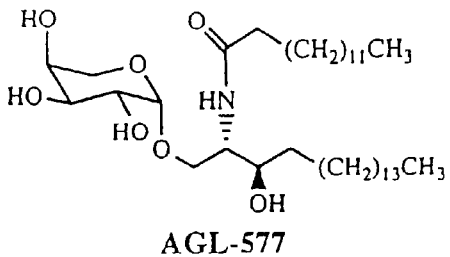
Figure 9:
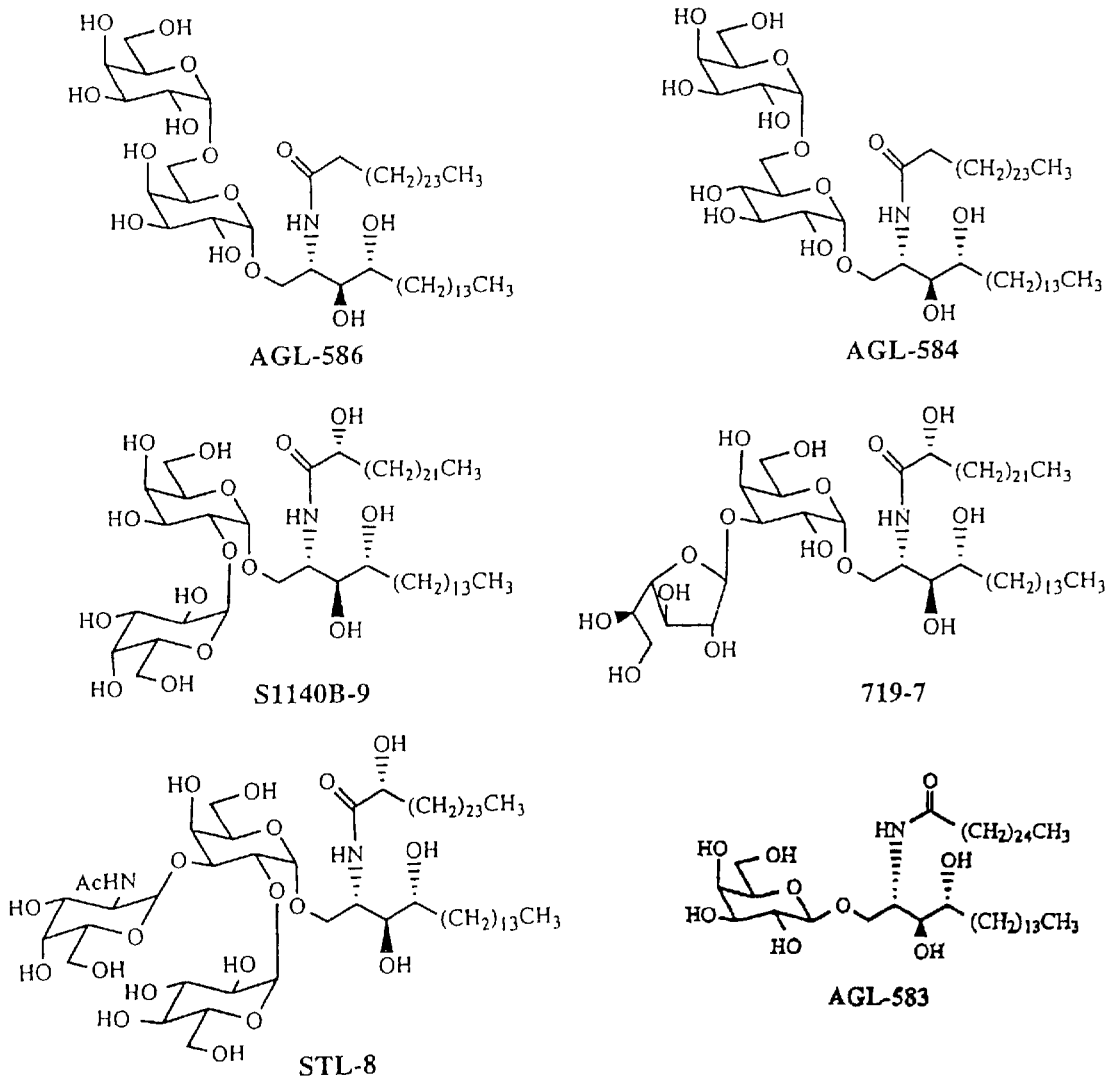
FIG. 9 shows chemical formulas of the compounds in Examples 1 to 3 and is the continuation of FIG. 8.

The synthesizing steps are shown in FIGS. 6 and 7.

(1) Synthesis of Compound G1

Sulfuric acid (0.5 ml) was added to a solution of D-lyxose (200 g, 1.33 mol) in acetone (3.0 L), which had been dried with calcium chloride, and the admixture was stirred for 18 hours at a room temperature. Molecular sieves 4A powder (100 g) was added, the reaction mixture was neutralized, then filtered with Celite, and the resulting residue was washed with acetone. The filtrate and the wash were combined and concentrated under vacuum to obtain a crude product of G1. Yield 240 g (95%). The product was used for the next step without further purification. A sample for assay was purified by silica gel chromatography using hexane:acetone (9:1) as the eluting solvent.

mp76–78° C.; FDMS m/z 191(M+1)$^+$; $^1$H-NMR(500 MHz,CDCl$_3$) δ5.45(1H,d,J=1.8 Hz),4.83(1H,dd,J=3.7,5.5 Hz),4.64(1H,d,J=6.1H z),4.27–4.30(1H,m),3.90–3.99(2H, m),1.48(3H,s), 1.32(3H,s)

(2) Synthesis of Compound G2

Pyridine (10 ml) and trityl chloride (39.0 g) were added to a methylene chloride solution (168 ml) of compound G1 (239 g, about 1.26 mmol), and the admixture was stirred for 4 hours at 32° C. Ethanol (8 ml) was added dropwise, and the admixture was stirred for 2 hours at a room temperature. After washing with an aqueous saturated ammonium chloride solution, an aqueous saturated sodium hydrogencarbonate solution and a saline solution, concentration under vacuum was carried out. The resulting residue was dissolved in ethyl acetate, cooled to 0° C. and then crystallized. Yield 501 g (87% from D-lyxose).

mp174–176° C.;FDMS m/z 432M$^+$; $^1$H-NMR(500 MHz, CDCl$_3$)δ7.21–7.49(15H,m), 5.38(1H,d,J=2.4 Hz), 4.75(1H, dd,J=3.7,6.1 Hz), 4.59(1H,d,J=6.1 Hz),4.31–4.35(1H,m), 3.43(1H,dd,J=4.9, 9.8 Hz),3.39(1H,dd,J=6.7,9.8 Hz), 1.29 (3H,s), 1.28(3H,s)

(3) Synthesis of Compound G3

To a THF solution (1500 ml) of tridecanetriphenylphosphonium bromide (962 g, 1.16 mol; prepared by heating 1-bromotridecane and triphenylphosphine for 4.5 hours at 140° C.), a 2.5 M hexane solution of n-butyl lithium (462 ml, 366 mmol) was added dropwise at 0° C. under an argon atmosphere. The admixture was stirred for 15 minutes, then a THF solution (450 ml) of compound G2 (250 g, 579 mmol) was added dropwise. This admixture was stirred for 18 hours while gradually raising the temperature to room temperature. The reaction solution was concentrated under vacuum, a mixture of hexane:methanol:water (10:7:3, 1000 ml) was added to the residue, and the admixture was washed with an aqueous saturated ammonium chloride solution. The water layer was extracted with hexane (500 ml). All the organic layers were combined, dried over anhydrous magnesium sulfate, and then concentrated under vacuum to obtain a crude product of compound G3. The product was used for the next step without further purification. Yield 339 g (98%). A sample for assay was purified by silica gel chromatography using hexane:ethyl acetate (9:1) as the eluting solvent.

FDMS m/z 598M$^+$; $^1$H-NMR(500 MHz,CDCl$_3$) δ7.21–7.45(15H,m), 5.48–5.59(2H,m),4.91(0.7H,t,J=7.3 Hz),4.44(0.3H,t,J=7.3 Hz), 4.26(0.3H,dd,J=4.3,7.3 Hz),4.21 (0.7H,dd,J=4.3,6.7 Hz), 3.75(0.7H,m),3.69(0.3H,m),3.24 (0.3H,dd,J=4.9,9.8 Hz),3.17(0.7H,dd,J=4.9,9.8 Hz), 3.09–3.14[1H,(3.11,dd,J=4.9,9.2 Hz), H1bEoverlapped], 1.75–2.03(2H,m),1.49(3H,s),1.39 and 1.38 (3H,each s),1.21–1.34 (20H,m),0.88(3H,t,J=6.7 Hz)

(4) Synthesis of Compound G4

To a methylene chloride solution (1500 ml) of compound G3 (338 g, about 565 mol), pyridine (500 ml) was added, and methanesulfonyl chloride (49 ml, 633 mmol) was added dropwise. The admixture was stirred for 24 hours at 31° C. Ethanol (40 ml) was added dropwise and the admixture was stirred for 1 hour at a room temperature. After concentration under vacuum, a mixture of hexane:methanol:water (10:7:3, 1000 ml) was added to the residue for separation. The water layer was extracted 3 times with hexane (200 ml). All the organic layers were combined, dried over anhydrous magnesium sulfate, and then concentrated under vacuum to obtain a crude product of compound G4. The product was used for the next step without further purification. Yield 363 g (95%). A sample for assay was purified by silica gel chromatography using hexane:ethyl acetate (9:1) as the eluting solvent.

FDMS m/z 676M$^+$; $^1$H-NMR(500 MHz,CDCl$_3$) δ7.21–7.47(15H,m), 5.41(0.7H,ddd,J=5.5,9.2,11.0 Hz),5.32 (0.7H,bt,J=11.0 Hz),5.22(0.3H,bdd,J=9.2,15.0 Hz),5.02 (0.3H,dt,Jt=7.3 Hz,Jd=15.0 Hz),4.8(0.7H,ddd,J=3.1,5.5,7.9 Hz),4.73(0.7H,dd,J=5.5,9.8 Hz), 4.64–4.67(0.3H,m),4.61 (0.3H,dd,J=5.5,9.2 Hz), 4.48(0.7H,dd,J=5.5,7.9 Hz),4.22 (0.3H,dd,J=5.5,9.2 Hz), 3.55(0.3H,dd,J=2.4,11.6 Hz),3.45 (0.7H,dd,J=3.2,11.0 Hz), 3.06–3.12[4H,(3.12,s),(3.11,s), (3.09,dd,J=3.1,11.0 Hz)], 1.66–1.82(2H,m),1.47 and 1.46 (3H,each s),1.39(3H,s), 1.13–1.35(20H,m),0.88(3H,t,J=6.8 Hz)

(5) Synthesis of Compound G5

To a methylene chloride solution (1500 ml) of compound G4 (362 g, about 536 mol), methanol (350 ml) was added, then concentrated hydrochloric acid (200 ml) was added dropwise. The admixture was stirred for 5 hours at a room temperature. The reaction solution was neutralized by adding sodium hydrogencarbonate, then filtered. The filtrate was concentrated under vacuum and ethyl acetate was added to the resulting residue and washing was carried out with a saline solution. The water layer was extracted with ethyl acetate, all the organic layers were combined, dried over anhydrous magnesium sulfate, then concentrated under vacuum. Crystallization was carried out with hexane. Yield 161 g (70% from G2).

mp66–67° C.;FDMS m/z 377(M-H$_2$O)$^+$; $^1$H-NMR(500 MHz,CDCl$_3$+D$_2$O) δ5.86(0.3H,dt,Jt=7.3 Hz,Jd=14.7 Hz), 5.77(0.7H,dt,Jt=7.3,Jd=10. 4 Hz),5.55(0.3H,br.dd,J=7.3, 14.7 Hz),5.49(0.7H,bt,J=9.8 Hz),4.91–4.97(1H,m),4.51 (0.7H,bt,J=9.8 Hz),4.11(0.3H,bt, J=7.3 Hz),3.94–4.03(2H, m),3.67–3.73[1H,(3.70,dd,J=3.1, 6.7 Hz),(3.69,dd,J=3.1,7.3 Hz)],3.20 and 3.19(3H,each s),2.05–2.22(2H,m),1.22–1.43 (20H,m),0.88(3H,t,J=6.7 Hz)

(6) Synthesis of Compound G6

To a THF solution (780 ml) of compound G5 (160 g, about 405 mol), 5% palladium-barium sulfate (16 g) was added. After replacing the air in a reaction chamber with hydrogen gas, the admixture was stirred for 20 hours at a room temperature. The reaction solution was filtered using Celite, then washed with a mixture of chloroform:methanol (1:1). The filtrate and wash were combined and concentrated under vacuum. The resulting residue was crystallized with ethyl acetate. Yield 146 g (91%).

[α]$^{23}_D$+12°(c1,CHCl$_3$/MeOH=1:1);mp124–126° C.;FDMS m/z 397(M+1)$^+$;$^1$H-NMR(500 MHz,CDCl$_3$/ CD$_3$OD=1:1)δ4.93–4.96(1H,m, H2),3.91(1H,dd,J=6.7,12.2 Hz),3.85(1H,dd,J=4.9,12.2 Hz),3.54–3.60(1H,m),3.50 (1H, dd,J=1.8,8.5 Hz), 3.19 (3H,s),1.75–1.83(1H,m),1.53–1.62 (1H,m),1.21–1.45(24H,m),0.89 (3H,t,J=6.7 Hz)

(7) Synthesis of Compound G7

To a DMF solution (1000 ml) of compound G6 (145 g, 365 mol), sodium azide (47 g, 730 mmol) was added, and the admixture was stirred for 4 hours at 95° C. The reaction solution was concentrated, ethyl acetate was added to the resulting residue and washing was carried out with water. The water layer was extracted again with ethyl acetate. All the organic layers were combined, washed with a saline solution, dried over anhydrous magnesium sulfate, and then concentrated under vacuum to obtain a crude product of compound G7. Yield 122 g (97%). The product was used for the next step without further purification. Yield 126 g (95%). A sample for assay was purified by silica gel chromatography using hexane:ethyl acetate (9:1) as the eluting solvent.

[α]$^{23}_D$+16.5°(c0.5,CHCl$_3$—MeOH,1:1);mp92–93° C.;FDMS m/z 344(M+1)$^+$; $^1$H-NMR(500 MHz,CD$_3$OD) δ3.91(1H,dd,J=3.7,11.6 Hz), 3.75(1H,dd,J=7.9,11.6 Hz), 3.49–3.61(3H,m),1.50–1.71(2H,m), 1.22–1.46(24H,m), 0.90(3H,t,J=6.7 Hz)

(8) Synthesis of Compound G8

To a methylene chloride solution (750 ml) of compound G7 (121 g, about 352 mmol), pyridine (250 ml) and trityl chloride (124 g, 445 mmol) were added, and the admixture was stirred for 16 hours at a room temperature. Ethanol (30 ml) was added dropwise. The admixture was stirred for 30 minutes at a room temperature, washed with an aqueous saturated sodium hydrogencarbonate solution, an aqueous saturated ammonium chloride solution and a saline solution, dried over anhydrous magnesium sulfate, and then concentrated under vacuum. The residue was purified by silica gel chromatography using hexane:ethyl acetate (10:1) as the eluting solvent. Yield 34.4 g (52% from G6).

[α]$^{24}_D$+11.9°(c0.9,CHCl$_3$),FDMS m/z 585M$^+$; $^1$H-NMR (500 MHz,CDCl$_3$+D$_2$O)δ7.24–7.61(15H,m),3.62–3.66(2H, m), 3.51–3.57(2H,m),3.42(1H,dd,J=6.0,10.4 Hz),1.23–1.56 (26H,m), 0.88(3H,t,J=6.7 Hz)

(9) Synthesis of Compound G9

To a DMF solution (300 ml) of compound G8 (33.5 g, 57.3 mmol), 60% hydrogenated sodium (5.5 g, about 138 mmol as NaH) was added, and the admixture was stirred for 40 minutes at a room temperature. The reaction solution was cooled to 0° C. and benzyl chloride (15 ml, 120 mmol) was added dropwise. The admixture was stirred for 18 hours while gradually raising the temperature to a room temperature. Ice water (100 ml) was added to the reaction solution. After the reaction was stopped, extraction was carried out using ethyl acetate. The extract was washed 3 times with a saline solution, and all the organic layers were combined, dried over anhydrous magnesium sulfate, and then concentrated under vacuum to obtain a crude product of compound G9. The product was used for the next step without further purification. Yield 42.2 g (96%). A sample for assay was purified by silica gel chromatography using hexane:ethyl acetate (100:1) as the eluting solvent.

$[\alpha]^{24}_D$+9.8°(c1.0,CHCl$_3$),FDMS m/z 738(M-N$_2$)$^+$; $^1$H-NMR(500 MHz, CDCl$_3$)δ7.07–7.48(25H,m),4.57(1H,d, J=11.6 Hz),4.44(1H,d, J=11.6 Hz),4.41(2H,s),3.73–3.79 (1H,m),3.46–3.56(2H,m),3.37 (1H,dd,J=8.6,10.4 Hz), 1.20–1.64(26H,m),0.88(3H,t,J=6.7 Hz)

(10) Synthesis of Compounds G10 and G11

To a 1-propanol solution (250 ml) of compound G9 (41.2 g, about 54 mmol), methanol (30 ml) was added, and further 5% palladium carbon (4.1 g) and ammonium formate (27.1 g, 4.3 mol) were added. After stirring for 16 hours at a room temperature, the admixture was diluted with ethyl acetate and filtered with Celite. The filtrate was concentrated under vacuum, and the resulting residue was dissolved with ethyl acetate and washed 3 times with an aqueous saturated sodium hydrogencarbonate solution and a saline solution. All the organic layers were combined, dried over anhydrous magnesium sulfate, and then concentrated under vacuum to obtain a crude product of G10. Yield 38.9 g (98%). G10 thus obtained was used for the next step without further purification.

To a methylene chloride solution (300 ml) of compound G10, hexacosanoic acid (22.4 g, 56.5 mmol) and WSC hydrogenchloride (12.6 g, 64.6 mmol) were added, and the admixture was fluxed for 2 hours while heating. The mixture was cooled to room temperature and concentrated under vacuum. Ethyl acetate (500 ml) was added to the residue, and washing was carried out with an aqueous 0.5 M hydrochloric acid solution, a saline solution, and an aqueous saturated sodium hydrogencarbonate solution, and further with a saline solution. All the organic layers were combined, dried over anhydrous magnesium sulfate, and then concentrated under vacuum to obtain a crude product of compound G11. Yield 53.2 g (88%). G11 thus obtained was used for the next step without further purification. A sample for assay was purified by silica gel chromatography using hexane-:ethyl acetate (100:1) as the eluting solvent.

$[\alpha]^{24}_D$+5.3°(c0.4,CHCl$_3$);FDMS m/z 1118M$^+$; $^1$H-NMR (500 MHz, CDCl$_3$) δ7.20–7.38(25H,m),5.57(1H,d,J=9.1 Hz),4.80(1H,d, J=11.6 Hz),4.48–4.50(3H,m),4.24–4.32(1H, m),3.83(1H,dd, J=3.0,6.7 Hz),3.43–3.51 (2H,m,H1a), 3.29 (1H,dd,J=4.3,9.8 Hz), 1.92(2H,t,J=7.3 Hz), 1.28–1.60(72H, m), 0.88(6H,t,J=6.7 Hz)

(11) Synthesis of Compound G12

To a methylene chloride solution (180 ml) of compound G11 (52.2 g, about 47 mmol), methanol (36 ml) was added, then a 10% methanol chloride solution (3.0 ml) was added dropwise, and the admixture was stirred for 2 hours at a room temperature. The reaction solution was neutralized with sodium hydrogencarbonate powder (18 g) and filtered with Celite. The residue was washed with methylene chloride. The filtrate and wash were combined and washed with a saline solution. The organic layer was dried over anhydrous magnesium sulfate, and then concentrated under vacuum. The residue was dissolved in acetone while heating, and the solution was cooled to 0° C. and purified by precipitation. Yield 38.6 g (77% from G9).

$[\alpha]^{24}_D$−29.7°(c0.7,CHCl$_3$);mp75–76.5° C.;FDMS m/z 876M$^+$; $^1$H-NMR (500 MHz,CDCl$_3$)δ7.30–0.47(10H,m), 6.03(1H,d,J=7.9 Hz),4.72(1H,d,J=11.6 Hz),4.66(1H,d,J= 11.6 Hz),4.61(1H,d,J=11.6 Hz),4.45(1H,d,J=11.6 Hz), 4.12–4.17(1H,m),4.00(1H,dt,Jt=4.3, Jd=7.3 Hz),3.67–3.72 (2H,m),3.61(1H,ddd,J=4.3,8.6,11.6 Hz), 1.94–2.05(2H,m), 1.15–1.69 (72H,m),0.88(6H,t,J=6.1 Hz)

(12) Synthesis of Compound G13

1) 2,3,4,6-tetra-O-benzyl-D-galactopyranosylacetate (79.8 g) was dissolved in a mixture of toluene (160 ml) and isopropyl ether (520 ml), and the solution was cooled to −10 to 0° C. To this solution, an isopropyl ether solution (2.8 mmol/ml, about 100 ml) containing 2.0 equivalent volumes of HBr was added. After stirring for about 90 minutes at −10° C. to 0° C., an aqueous 5% sodium hydrogencarbonate solution was poured into the reaction solution, and excessive HBr was neutralized by stirring. The whole volume was transferred into a separation funnel for separation, then the water layer was discarded and washing was carried 2 times with an aqueous 10% sodium chloride solution. After concentration under vacuum, 2,3,4,6-tetra-O-benzyl-α-D-galactopyranosyl bromide (GalBr) was obtained as a syrup.

2) DMF (140 ml), then a toluene solution (250 ml) of GalBr (about 137 mmol) were added to a toluene solution (420 ml) of compound G12 (60.0 g, 68.6 mmol), tetrahexylammonium bromide (89.4 g, 206 mmol) and molecular sieves 4A (60 g). The admixture was stirred for 72 hours at a room temperature. Methanol (12 ml) was added to the reaction solution, and the admixture was stirred for 2 hours. Filtration with Celite and washing with an aqueous saturated sodium hydrogencarbonate solution and a saline solution were followed by drying on anhydrous magnesium sulfate and concentration under vacuum. Acetonitrile was added to the resulting residue and the admixture was stirred for 2 hours. The resulting precipitate was dried under vacuum to obtain a dry powder. This powder was purified by silica gel chromatography using hexane:ethyl acetate (8:1) as the eluting solvent. Yield 70.9 g (74%).

$[\alpha]^{24}_D$+18.8°(c0.9,CHCl$_3$);mp74–75° C.;FDMS m/z 1399(M+1)$^+$; $^1$H-NMR(500 MHz,CDCl$_3$)δ7.21–7.37(30H, m),6.12(1H,d,J=9.0 Hz), 4.91(1H,d,J=11.6 Hz),4.84(1H,d, J=3.7 Hz),4.72–4.80(4H,m),4.35–4.65(7H,m),4.12–4.18 (1H,m),3.99–4.05(2H,m),3.84–3.93(4H,m), 3.73(1H,dd,J= 3.7,11.0 Hz),3.47–3.51(2H,m),3.42(1H,dd,J=6.1, 9.1 Hz), 1.87–1.99 (2H,m),1.18–1.70(72H,m),0.88(6H,t,J=7.4 Hz)

(13) Synthesis of Compound KRN 7000

Compound G13 (60.0 g, 42.9 mmol) was added to ethanol (960 ml) to make a suspension, to which an ethanol suspension of 20% hydroxy palladium (6.0 g) was added. Further, a hydrogen source, 4-methylcyclohexene (120 ml, 93.5 mmol) was added. After fluxing for 4 hours while heating, filtration was carried out, and the solvent was removed. The residue was washed with heated ethanol. The filtrate was allowed to stand at a room temperature to obtain a white precipitate, and the precipitate was filtered and dried under vacuum. The resulting powder was suspended in ethanol:water (92:8, 3.5 L) and dissolved by heat while stirring. The solution was allowed to stand to obtain a precipitate again. The solution with the precipitate was filtered, and the filtrated cake was dried under vacuum to obtain a white powder. Yield 35.0 g (95%).

$[\alpha]^{23}_D$+43.6°(c1.0,pyridine);mp189.5–190.5° C.; negative FABMS m/z 857 (M-H)$^-$;IR(cm$^{-1}$,KBr)3300,2930, 2850,1640,1540, 1470,1070;$^1$H-NMR(500 MHz,C$_5$D$_5$N) δ8.47(1H,d,J=8.5 Hz), 5.58(1H,d,J=3.7 Hz),5.27(1H,m), 4.63–4.70(2H,m),4.56(1H,m), 4.52(1H,t,J=6.1 Hz), 4.37–4.47(4H,m),4.33(2H,m),2.45(2H,t, J=7.3 Hz), 2.25–2.34(1H,m),1.87–1.97(2H,m),1.78–1.85(2H,m), 1.62–1.72(1H,m),1.26–1.45(66H,m),0.88(6H,t,J=6.7 Hz), $^{13}$C-NMR(125 MHz,C$_5$D$_5$N)δ173.2(s),101.5(d),76.7(d), 73.0(d),72.5(d), 71.6(d),71.0(d),70.3(d),68.7(t),62.7(t),51.4 (d),36.8(t),34.4(t),32.1(t),30.4(t),30.2(t),30.03(t),30.00(t), 29.93(t),29.87(t),29.81(t),29.76(t),29.6(t),26.5(t),26.4(t), 22.9(t),14.3(q)

Example 2

Isolation and Purification of O-α-D-galactopyranosyl-(1→2)-O-α-D-galactopyranosyl-(1→1)-(2S,3S,4R)-2-amino-N-[(R)-2-hydroxytetracosanoyl]-1,3,4-octadecanetriol (S1140B-9)

A freeze dried powder (447.1 g) of sponges, which were harvested at a depth of 15 to 25 m from the sea near Kume Island of Okinawa Prefecture, was extracted with a mixture of chloroform and methanol, then the extracted liquid was concentrated under vacuum to obtain 51.28 g of extract. The extract was partitioned with ethyl acetate and water, and the upper layer and the middle layer were dried over anhydrous sodium sulfate and concentrated under vacuum to obtain 18.37 g and 9.44 g of fractions, respectively. An alcohol layer, which was obtained by partitioning the fraction obtained from the upper layer with 10% aqueous methanol and n-hexane, and the fraction obtained from the middle layer were combined and concentrated. By repeating silica gel chromatography, 169.9 mg of a single active component on normal phase TLC was obtained. Further purification was carried out by reversed phase HPLC using an ODS-AM column (a product of YMC, 250 mm×20 mm diameter, methanol, 9.0 ml/min) (retention time: 30.3 minutes) to obtain 10.2 mg of the purified title compound (S1140B-9).

The title compound can also be isolated and purified by the method described in F. Cafieri et al., Liebigs Ann. Chem. 1995, 1477–1481.

negative FABMS m/z 1007[(M-H)$^-$];IR;$^1$HNMR(500 MHz,C$_5$D$_5$N,24° C.) δ(ppm)8.55(1H,d,J=9.2 Hz,NH),5.60 (1H,d,J=3.7 Hz,H1''),5.57(1H,d,J=3.7 Hz,H1'''),5.13(1H,m, H2),4.75(1H,dd,J=3.7,10.4 Hz,H2''),4.62(2H,m),4.54(4H, m),4.25–4.47(10H,m), 2.17(2H,m),1.99(1H,m),1.87(2H,m), 1.75(1H,m),1.65(2H,m),1.12–1.49(60H,m),0.85(6H,m, terminal methyl);

$^{13}$CNMR(125 MHz,C$_5$D$_5$N,45° C.)δ(ppm)175.5(s,C1'), 99.5(d,C1'''),98.6(d,C1''),76.7(d,C2''),76.0(d,C3),72.8(d, C4),72.6(d,C5''),72.6(d,C4''),72.5(d,C2),71.3(d,C3'''),71.0 (d),70.8(d),70.5(d,C2'''),69.7(d,C3''),68.6(t,C1),62.7(t),62.5 (t), 51.2(t,C2),39.4(t),35.6(t),33.7(t),32.2(t),30.5(t),30.3(t), 30.1(t),30.0(t),29.7(t),29.6(t),26.7(t),26.0(t),23.0(t),22.9(t), 14.3(q,terminal methyl)

Example 3

The following compounds were synthesized according to the methods described in the references given on the right column.

| Compound name | Reference |
|---|---|
| (2S,3R)-1-(α-D-galactopyranosyloxy)-2-tetradecanoylamino-3-octandecanol (AGL-517) | WO93/5055 |
| (2S,3R)-1-(α-D-glucopyranosyloxy)-2-tetradecanoylamino-3-octadecanol (AGL-563) | WO94/9020 |
| (2S,3R)-1-(6'-deoxy-α-D-galactopyranosyloxy)-2-tetradecanoylamino-3-octadecanol (AGL-571) | WO94/9020 |
| (2S,3R)-1-(β-L-arabinopyranosyloxy)-2-tetradecanoylamino-3-octadecanol (AGL-577) | WO94/9020 |
| O-α-D-galactopyranosyl-(1→6)-O-α-D-galacto pyranosyl-(1→1)-(2S,3S,4R)-2-amino-N-hexacosanoyl-1,3,4-octadecanetriol (AGL-586) | WO94/24142 |
| O-α-D-galactopyranosyl-(1→6)-O-α-D-gluco pyranosyl-(1→1)-(2S,3S,4R)-2-amino-N-hexacosanoyl-1,3,4-octadecanetriol (AGL-584) | WO94/24142 |
| O-α-D-galactofuranosyl-(1→3)-O-α-D-galacto pyranosyl-(1→3)-O-α-D-galactopyranosyl-(1→1)-(2S,3S,4R)-2-amino-N-[(R)-2-hydroxy tetracosanoyl]-1,3,4-octadecanetriol (719-7) | WO94/24142 |
| O-(N-acetyl-2-amino-2-deoxy-α-D-galacto pyronosyl-(1→3)-O-α-D-glucopyranosyl-(1→2)]-O-α-D-galactopyranosyl-(1→1)-(2S,3S,4R)-2-amino-N-[(R)-2-hydroxytetra-cosanoyl]-1,3,4-octadecanetriol (STL-8) | WO94/24142 |
| (2S,3S,4R)-1-(β-D-galactopyranosyloxy-2-hexacosanoylamino-3,4-octadecanediol (AGL583) | Bioorganic & Medicinal Chemistry Letters, Vol. 5, No. 7, pp 699–704 (1995) |

Relations between compounds of formula (I) and the compounds described in the example mentioned above are shown in Table 1.

TABLE 1

|  | X | R1 | R2 | R3 | R4 | R5 | R6 | R7 | R8 | R9 |
|---|---|---|---|---|---|---|---|---|---|---|
| KRN7000 | 23 | H | (b)Y = 13 | H | OH | OH | H | OH | H | CH$_2$OH |
| AGL517 | 11 | H | (a)Y = 13 | H | OH | OH | H | OH | H | CH$_2$OH |
| AGL563 | 11 | H | (a)Y = 13 | H | OH | OH | H | H | OH | CH$_2$OH |
| AGL571 | 11 | H | (a)Y = 13 | H | OH | OH | H | OH | H | CH$_3$ |
| AGL577 | 11 | H | (a)Y = 13 | H | OH | OH | H | OH | H | H |

TABLE 1-continued

| | X | R1 | R2 | R3 | R4 | R5 | R6 | R7 | R8 | R9 |
|---|---|---|---|---|---|---|---|---|---|---|
| AGL586 | 23 | H | (b)Y = 13 | H | OH | OH | H | OH | H | Group (A') |
| AGL584 | 23 | H | (b)Y = 13 | H | OH | OH | H | H | OH | Group (A') |
| S1140B-9 | 21 | OH | (b)Y = 13 | H | Group (A) | OH | H | OH | H | CH$_2$OH |
| 719-7 | 21 | OH | (b)Y = 13 | H | OH | Group (E) | H | OH | H | CH$_2$OH |
| STL-8 | 23 | OH | (b)Y = 13 | H | Group (B) | Group (F) | H | OH | H | CH$_2$OH |

Biological Test

Pharmacological Test 1

Effect of α-glycosylceramide on Immunogenicity of Tumor Cells

The experiment was carried out using C57BL/6 mice purchased from Japan SLC, Inc. The compound synthesized in Example 1 (KRN 7000) was used in the following experiment as a representative compound having an α-glycosylceramide structure. AGL-583, the compound synthesized in Example 3 having a β-glycosylceramide structure, was used as a negative control.

First, the effect of a vehicle, KRN 7000, and AGL-583 on immunogenicity of tumor cells was studied. Tumor cells, mouse T lymphoma EL-4 cells (Dainippon Pharmaceutical Co., Ltd.), were suspended in an RPM11640 medium containing 10% FCS (fetal calf serum), glutamine and antibiotics, and cultured in vitro. Before starting the treatment with each drug, EL-4 cells were recovered and suspended again in a fresh medium, then incubation was started immediately with an addition of a vehicle (0.1% DMSO), KRN 7000 (100 ng/ml) or AGL-583 (100 ng/ml). One day after incubation, three kinds of tumor cells, i.e., EL-4/V, EL-4/KRN and EL-4/583, cultured in the presence of the vehicle, KRN 7000 and AGL-583, respectively, were harvested, washed twice with the medium, then suspended again in the fresh medium. The suspensions were immunized intravenously into the tail of C57BL/6 mice (females, 8 weeks of age), at 5×10$^5$ cells/mouse. Three days later, spleen cell fractions were prepared as effector cells from (1) mice without immunization (healthy control), (2) mice inoculated with EL-4/V, (3) mice immunized with EL-4/KRN and (4) mice immunized with EL-4/583. As target cells, $^{51}$Cr-labeled YAC-1 (Dainippon Pharmaceutical Co., Ltd.) and EL-4 murine tumor cells were used. The effector cells and target cells were plated at an E/T (effector/target) ratio of 25:1, 50:1 and 100:1. After incubating for 4 hours, released $^{51}$Cr was measured by a γ-counter to calculate cytotoxic activity of respective spleen cells using the following formula.

$$\text{Cytotoxic activity (\%)} = \frac{\text{Experimental release} - \text{Spontaneous release}}{\text{Maximum release} - \text{Spontaneous release}} \times 100$$

"Maximum release" means the amount of $^{51}$Cr released when cultured with an addition of HCl, "spontaneous release" means the amount of $^{51}$Cr released when cultured with no addition, and "experimental release" means the amount of $^{51}$Cr released when individual spleen cells were added. Results are shown in FIG. 1.

As shown in FIG. 1A, cytotoxic activity to YAC-1 in spleen cells of mice immunized with EL-4/V and EL-4/583 were almost the same as that in those of healthy mice. In contrast, spleen cells of mice immunized with EL-4/KRN showed remarkably high cytotoxic activity.

On the other hand, as shown in FIG. 1B, cytotoxic activity to EL-4 was higher in spleen cells of mice immunized with EL-4/V or EL-4/583 than in those of healthy control mice, but cytotoxic activity was further higher in spleen cells of mice inoculated with EL-4/KRN.

The results above reveal that incubation of tumor cells with the addition of an α-glycosylceramide enhances immunogenicity of the tumor cells so that an extremely strong tumor immunity is induced in mice inoculated with the resulting tumor cells. Furthermore, although an immunity to EL-4, namely an anti-tumor immunity only to a specific tumor, was induced at a low level in spleen cells of mice immunized with EL-4/V or EL-4/583, an extremely strong tumor immunity against not only EL-4 but also NK-sensitive YAC-1 cells was induced in spleen cells in mice immunized with EL-4/KRN. Accordingly, it was revealed that not only tumor-specific immunity but also non-specific immunity was induced by the immunization with EL-4/KRN.

Pharmacological Test 2

Therapeutic Effect of Tumor Cells Treated with α-glycosylceramide on ET-4 Liver Metastasis Model Mice Since the results of Pharmacological Test 1 revealed that α-glycosylceramides were effective to enhance immunogenicity of tumor cells, we next studied whether immunization of α-glycosylceramide-treated tumor cells exerts an antitumor effect on existing tumors, i.e., the immunization of immunogenicity-enhanced tumor cells is effective in tumor therapy.

Mouse T lymphoma EL-4 cells (4×10$^5$ cells/mouse) were implanted intravenously into the tail of BDF1 mice (female, 6 weeks of age, Japan SLC, Inc.), 6 animals in one group, to prepare cancer-bearing mice. The days of tumor implantation was set to be day 0. On the same day, a vehicle (0.1% DMSO), KRN 7000 (100 ng/ml) or AGL-583 (100 ng/ml) was added to EL-4 cells which had been inoculated into a fresh medium, in the same manner as in Pharmacological Test 1 above. One day after the start of incubation, cells of EL-4/V, EL-4/KRN and EL-4/583 cultured in the presence of the vehicle, KRN 7000 and AGL-583, respectively, were recovered and washed twice with the medium, after which the recovered cells were immunized intravenously into the tail of the cancer-bearing mice at 1×10$^5$ cells/mouse. The resulting antitumor effect was compared.

EL-4 implanted mice generally died in about 30 days owing to the tumor formation and growth in several organs, particularly in the liver. Therefore, antitumor effect was evaluated by observing the survival period of cancer-bearing hosts. Results are shown in FIG. 2.

As shown in FIG. 2, in EL-4-bearing mice immunized with EL-4 treated with vehicle or AGL-583, the survival period was not prolonged at all and no evident antitumor effect was observed, as compared to control mice into which only tumors were implanted. In contrast, in EL-4-bearing mice immunized with KRN7000-treated EL-4, the survival period was markedly prolonged and 33.3% of treated mice survived for a long term.

The results above show that while tumor cells treated with the vehicle or AGL-538, a compound having a β-glycosylceramide structure, has no effect when applied in tumor therapy, tumor cells cultured with an addition of KRN 7000, a compound having an α-glycosylceramide structure, have marked antitumor activities when applied in tumor therapy. Thus, it was revealed that tumor cells treated with an α-glycosylceramide was effective in tumor therapy.

Pharmacological Test 3

Therapeutic Effect of Tumor Cells Treated with α-glycosylceramide on B16 Melanoma Lung Metastasis Model Mice Tumor cells other than those used in Pharmacological Test 2, i.e., B16 melanoma (Dainippon Pharmaceutical Co., Ltd.), were treated with an α-glycosylceramide to study effectiveness of these tumor cells in tumor therapy.

Mouse B16 melanoma cells ($4 \times 10^5$ cells/mouse) were implanted intravenously into the tail of BDF1 mice (females, 6 weeks of age), 6 animals in one group, to prepare cancer-bearing mice. The day of tumor implantation was set to be day 0. Incubation of B16 cells was started on the same day with an addition of a vehicle (0.1% DMSO) or KRN 7000 (100 ng/ml) in the same manner as in Pharmacological Test 2. One day after the incubation, cells of B16/V and B16/KRN cultured in the presence of the vehicle and KRN 7000, respectively, were harvested and washed twice with the medium. Then, the harvested cells were immunized intravenously into the tail of the above-mentioned cancer-bearing mice at $1 \times 10^5$ cells/mouse. The resulting antitumor effect was compared.

B16-implanted mice generally died in about 60 days owing to the formation and growth of metastatic nodules in lung. Accordingly, antitumor effect was evaluated by observing the survival period of cancer-bearing hosts. Results are shown in FIG. 3.

As shown in FIG. 3, in cancer-bearing mice immunized with B16/V cells, the antitumor effect was not observed at all and the survival period rather tended to be shortened as compared with the control mice into which only tumor cells were implanted. In contrast, in mice inoculated with B16/KRN, a marked antitumor effect was observed and 50% of the mice survived for 70 days after the tumor implantation.

The results above show that tumor cells other than those used in Pharmacological Test 2 treated with an α-glycosylceramide exert marked antitumor effects when immunized into cancer-bearing mice. Thus, it was revealed that tumor cells treated with an α-glycosylceramide were effective in tumor therapy.

Pharmacological Test 4

Effect of α-glycosylceramide on Tumorigenicity of Tumor Cells

Results of Pharmacological Tests 2 and 3 revealed that tumor cells treated with an α-glycosylceramide had antitumor activity on cancer-bearing mice. Generally, in conventional tumor therapy, proliferative activity of tumor cells are abrogated by radiation or other treatment before immunization, otherwise immunized tumor itself used as vaccine might formed tumor burden. In fact, the results of Pharmacological Test 3 showed that the survival period of mice immunized with tumor cells treated with the vehicle tended to be shortened, although very slightly. However, tumor cells treated with an α-glycosylceramide not only extended the survival period, but cases of a virtual cure were also noted. Therefore, α-glycosylceramide-treated tumor cells were considered to be used without abrogation of their proliferative ability by radiation or the like, but its tumorigenicity (the ability to form tumor burden)remained to be confirmed. Therefore, the effect of an α-glycosylceramide on tumorigenicity of various murine tumors was studied as follows.

Six kinds of mouse tumor cells, i.e., three kinds of C57BL/6 mouse-derived tumor cells, i.e., murine melanoma B16 cells (Dainippon Pharmaceutical Co., Ltd.), mouse T lymphoma EL-4 cells (Dainippon Pharmaceutical Co., Ltd.) and mouse Lewis lung carcinoma cells (Dainippon Pharmaceutical Co., Ltd.), and three kinds of BALB/c-mouse derived tumor cells, i.e., mouse colon cancer cell Colon 26 (Japanese Foundation for Cancer Research), mouse leukemia L1210 cells (Japanese Foundation for Cancer Research) and mouse fibrosarcoma Meth A cells (Japanese Foundation for Cancer Research) were cultured with or without an addition of a vehicle (0.1% DMSO) or KRN 7000 (100 ng/ml) for one day as described in Pharmacological Tests above. The resulting tumor cells were washed twice with a medium, suspended again in a fresh medium and implanted intravenously into the tail of corresponding mice. That is, B16, EL-4 and LLC cells were implanted to C57BL/6 mice (females, 9 weeks of age) at $5 \times 10^5$ cells/mouse, $1 \times 10^5$ cells/mouse and $5 \times 10^5$ cells/mouse, respectively; and Colon 26, Meth A, and L1210 cells were implanted to BALB/c mice (females, 9 weeks of age) at $2 \times 10^6$ cells/mouse, $1 \times 10^5$ cells/mouse and $5 \times 10^5$ cells/mouse, respectively.

The tumor cells implanted intravenously into the tail formed metastasized nodules in various organs, particularly in the liver or lung, and ultimately killed the animals. Accordingly, the effect of the tumor cells on tumorigenicity (a rate of tumor formation, the ability to form tumor burden) was evaluated by observing the survival period.

As shown in FIG. 4, all the mice implanted with tumor cells which were cultured in a common medium without any drug died and their tumorigenicity were 100%. Similarly, all the mice, immunized with tumor cells, which were cultured with vehicle for 1 day, died and their tumorigenicity were 100%. In contrast, 40 to 100% of mice implanted with tumor cells, which were cultured with KRN7000 for 1 day, survived and their tumorigenicity were diminished or completely abolished.

The results above show that tumorigenicity of tumor cells is markedly reduced by culturing with an addition of α-glycosylceramides represented by KRN 7000. A separate study was carried out to find out whether KRN 7000 had cytostatic activity against tumor cells. The results show that tumor cells cultured with an addition of KRN 7000 in the same manner as in Pharmacological Test 4 have a proliferative ability similar to tumor cells cultured with no addition or with an addition of the vehicle. Thus, it was revealed that the observed effect was not elicited by direct cytotoxicity of KRN7000 itself against tumor cells, but due to other biological activities.

Thus, it was revealed that tumor cells treated with an α-glycosylceramide can be immunized as a useful cancer vaccine, without further radiation to impair their proliferative ability. Accordingly, the results of Pharmacological Tests 1 to 4 suggest that when tumor cells treated with an α-glycosylceramide are immunized, the host's immunity almost completely eradicates the immunized tumor cells themselves, and at the same time, immunocompetent cells of the host are activated to induce antitumor immunity to the original existing tumors.

Tumor cells other than those used in Pharmacological Tests 1 to 3 were also used in this study. It was revealed that tumorigenicity of all the tumor cells was reduced by treating them with an α-glycosylceramide. Considering that the therapeutic effect of B16 and EL-4 cells treated with an α-glycosylceramide was closely associated with the reduction of tumorigenicity, tumor therapy with tumor cells other than B16 and EL-4 is also considered to be possible.

Pharmacological Test 5

Therapeutic Effect of Tumor Cells Treated with α-glycosylceramide and Radiated on B16 Melanoma Lung Metastasis Model Mice The results of Pharmacological Tests 2 to 4 revealed that tumor cells treated with an α-glycosylceramide were useful as a cancer vaccine without further treatment by radiation or chemotherapeutic agents or the like to kill the cells. However, safer tumor vaccines in which cells are killed by radiation or the like are generally used in ordinary tumor therapy. Accordingly, a study was carried out to see whether α-glycosylceramide-treated tumor cells exhibited therapeutic activity when these were irradiated before immunization.

Mouse B16 melanoma cells ($5 \times 10^5$ cells/mouse) were implanted intravenously into the tail of C57BL/6 mice (females, 9 weeks of age), 7 animals in one group, to prepare cancer-bearing mice. The day of tumor implantation was set to be day 0. On the same day, B16 cells suspended on a fresh medium were incubated in vitro with an addition of a vehicle (0.1% DMSO) or KRN 7000 (100 ng/ml) in the same manner as in Pharmacological Test 4. One day after incubation, B16/V and B16/KRN cells cultured in the presence of the vehicle and KRN 7000, respectively, were harvested and washed twice with PBS (phosphate buffered saline). Then, the resultant cells were divided into two groups, 200-Gy-irradiated or not irradiated, and immunized intravenously into the tail of the above-mentioned cancer-bearing mice at $1 \times 10^5$ cells/mouse. Antitumor effects of the two groups of the cells were compared.

As shown in FIG. 5, irrespective of radiation or non-radiation, no antitumor effect was observed in mice inoculated with V16/V cells, as compared to control mice inoculated with untreated tumor cells. Conversely, irrespective of radiation or non-radiation, a marked antitumor effect was observed in mice inoculated with V16/KRN cells, and about 60% to 70% of the mice survived up to 50 days after tumor implantation.

The results above show that irradiated α-glycosylceramide-treated tumor cells have marked antitumor activity similar to those without radiation, as in Pharmacological Tests 2 and 3. Thus, it was revealed that α-glycosylceramide-treated tumor cells can be further radiated to make them applicable for safer tumor therapy.

What is claimed is:

1. A method for treating tumors in a mammal in need thereof, comprising:

administering to the mammal an effective amount of the tumor cell that has been in in vitro contact with the compound of formula (I):

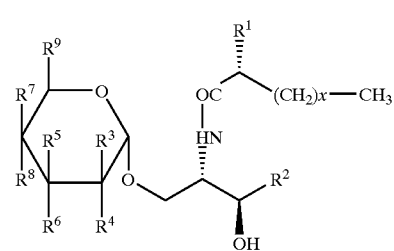

wherein $R^1$ represents H or OH,

X represents an integer between 7 and 27, $R^2$ represents a substituent selected from the group consisting of the following (a) to (e) (wherein Y represents an integer between 5 and 17):

(a) —$CH_2(CH_2)_YCH_3$
(b) —$CH(OH)(CH_2)_YCH_3$
(c) —$CH(OH)(CH_2)_YCH(CH_3)_2$
(d) —$CH=CH(CH_2)_Y(CH_3)$
(e) —$CH(OH)(CH_2)_YCH(CH_3)CH_2CH_3$, and $R^3$ to $R^9$ represent substituents as defined in any one of the following i) and ii):

i) when $R^3$, $R^6$ and $R^8$ represent H, $R^4$ represents H, OH, $NH_2$, $NHCOCH_3$, or a substituent selected from the group consisting of the following groups (A) to (D):

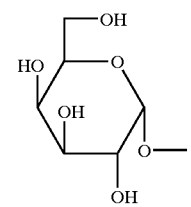

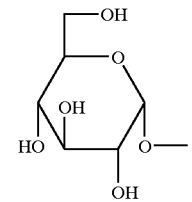

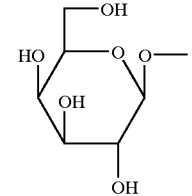

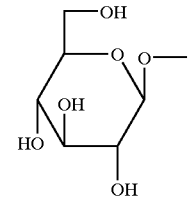

$R^5$ represents OH or a substituent selected from the group consisting of the following groups (E) and (F):

(E)
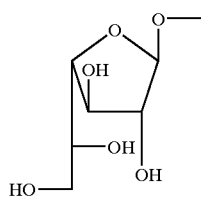

(F)
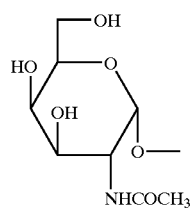

$R^7$ represents OH or a substituent selected from the group consisting of the following groups (A) to (D):

(A)
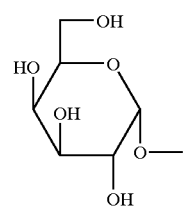

(B)
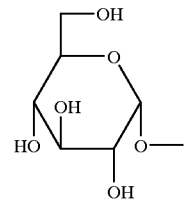

(C)
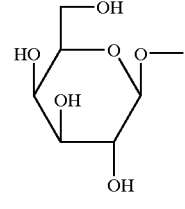

(D)
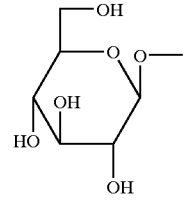

$R^9$ represents H, CH$_3$, CH$_2$OH or a substituent selected from the group consisting of the following groups (A') to (D'):

(A')
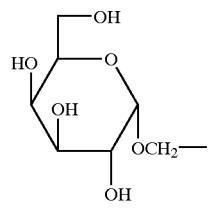

(B')
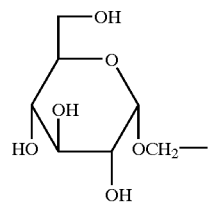

(C')
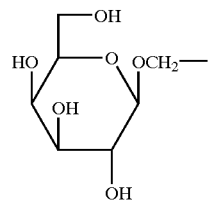

(D')
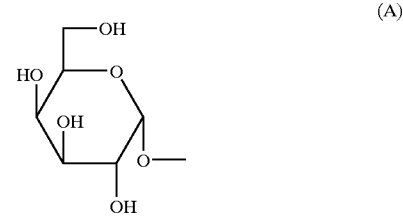

ii) when $R^3$, $R^6$ and $R^7$ represent H,
$R^4$ represents H, OH, NH$_2$, NHCOCH$_3$, or substituent selected from the group consisting of the following groups (A) to (D):

(A)
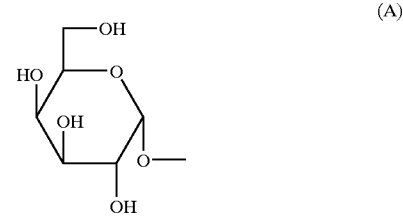

(B)
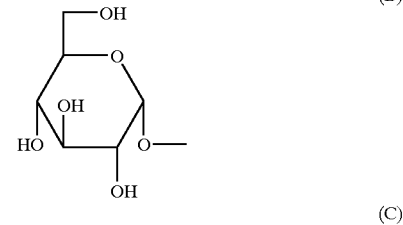

(C)
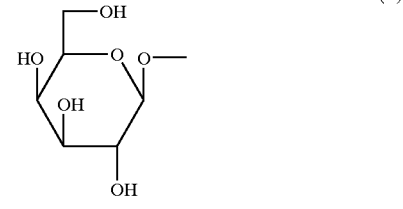

-continued

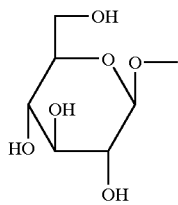
(D)

$R^5$ represents OH or a substituent selected from the group consisting of groups (E) and (F):

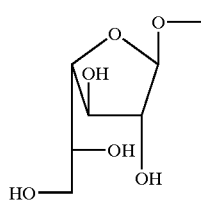
(E)

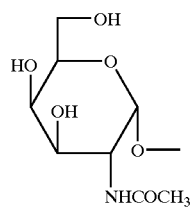
(F)

$R^8$ represents OH or a substituent selected from the group consisting of the following groups (A) to (D):

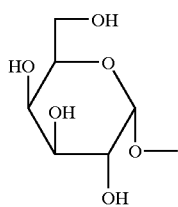
(A)

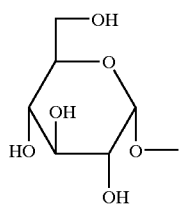
(B)

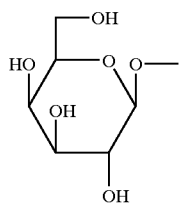
(C)

-continued

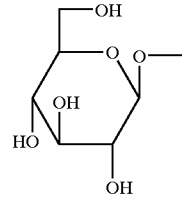
(D)

$R^9$ represents H, $CH_3$, $CH_2OH$ or a substituent selected from the group consisting of the following groups (A') to (D'):

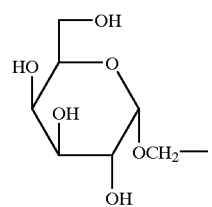
(A')

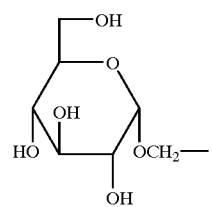
(B')

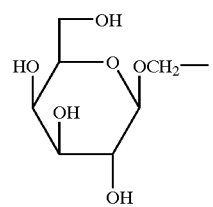
(C')

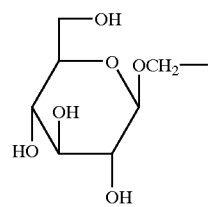
(D')

or a salt or solvate thereof.

2. The method of claim 1, wherein the administered tumor cells are melanoma or kidney cancer cells.

3. The method of claim 1, further comprising inactivating the tumor cell by radiation or a cytotoxic agent prior to administering.

4. A method for treating virus infections in a mammal in need thereof, comprising:

administering to the mammal an effective amount of the virus infected cell that has been in in vitro contact with the compound of formula (I):

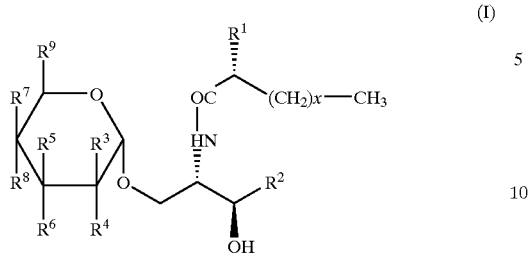
(I)

wherein
- $R^1$ represents H or OH,
- X represents an integer between 7 and 27,
- $R^2$ represents a substituent selected from the group consisting of the following (a) to (e) (wherein Y represents an integer between 5 and 17):
  - (a) —$CH_2(CH_2)_YCH_3$
  - (b) —$CH(OH)(CH_2)_YCH_3$
  - (c) —$CH(OH)(CH_2)_YCH(CH_3)_2$
  - (d) —$CH=CH(CH_2)_Y(CH_3)$
  - (e) —$CH(OH)(CH_2)_YCH(CH_3)CH_2CH_3$, and
- $R^3$ to $R^9$ represent substituents as defined in any one of the following i) and ii):
  - i) when $R^3$, $R^6$ and $R^8$ represent H,
    - $R^4$ represents H, OH, $NH_2$, $NHCOCH_3$, or a substituent selected from the group consisting of the following groups (A) to (D):

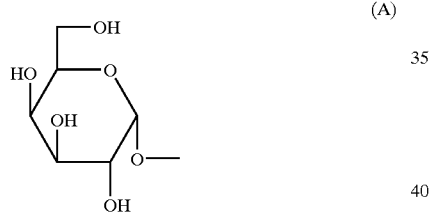
(A)

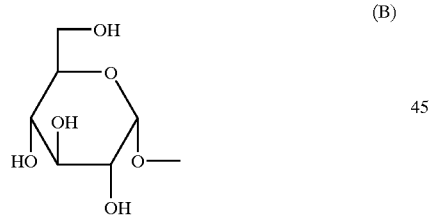
(B)

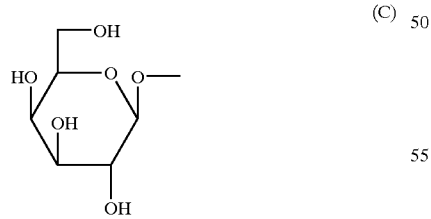
(C)

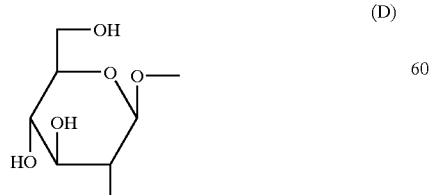
(D)

$R^5$ represents OH or a substituent selected from the group consisting of the following groups (E) and (F):

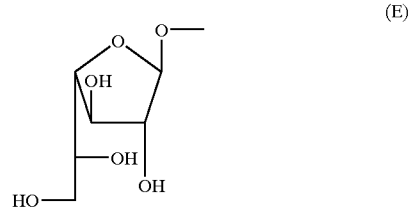
(E)

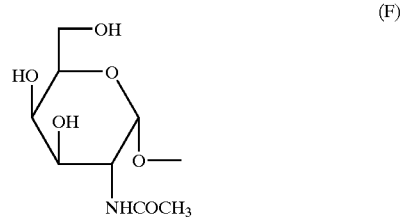
(F)

$R^7$ represents OH or a substituent selected from the group consisting of the following groups (A) to (D):

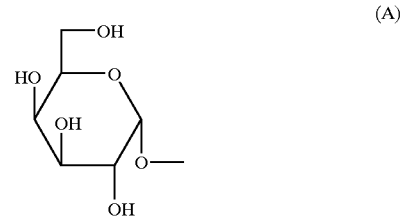
(A)

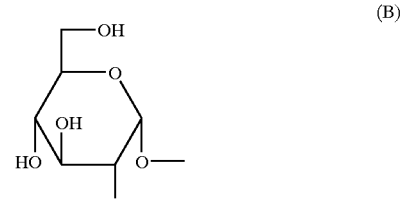
(B)

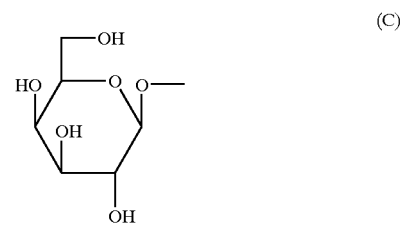
(C)

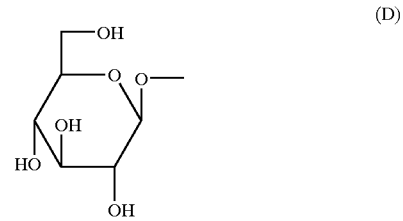
(D)

$R^9$ represents H, $CH_3$, $CH_2OH$ or a substituent selected from the group consisting of the following groups (A') to (D'):

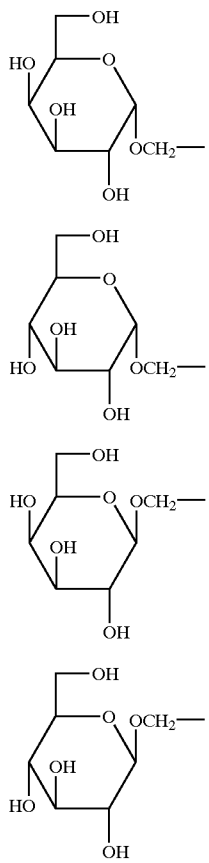
ii) when $R^3$, $R^6$ and $R^7$ represent H,
  $R^4$ represents H, OH, $NH_2$, $NHCOCH_3$, or substituent selected from the group consisting of the following groups (A) to (D):
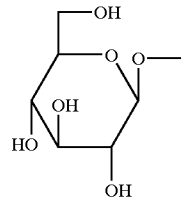
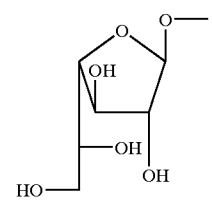
$R^5$ represents OH or a substituent selected from the group consisting of groups (E) and (F):
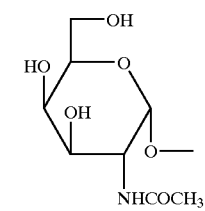
$R^8$ represents OH or a substituent selected from the group consisting of the following groups (A) to (D):
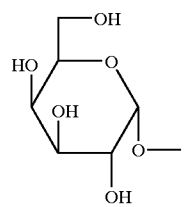
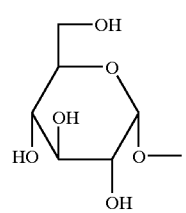
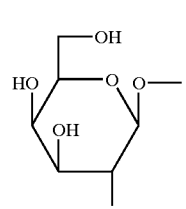

-continued

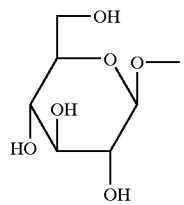
(D)

$R^9$ represents H, $CH_3$, $CH_2OH$ or a substituent selected from the group consisting of the following groups (A') to (D'):

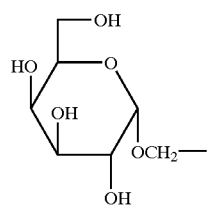
(A')

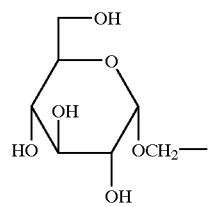
(B')

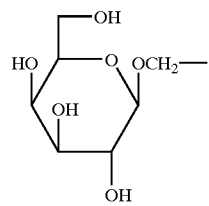
(C')

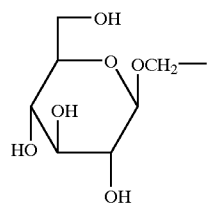
(D')

or a salt or solvate thereof.

5. The method of claim 4, further comprising inactivating the virus infected cell by radiation or a cytotoxic agent prior to administering.

6. A method for treating pathogen infections in a mammal in need thereof, comprising:

administering to the mammal an effective amount of the pathogen infected cell that has been in in vitro contact with the compound of formula (I):

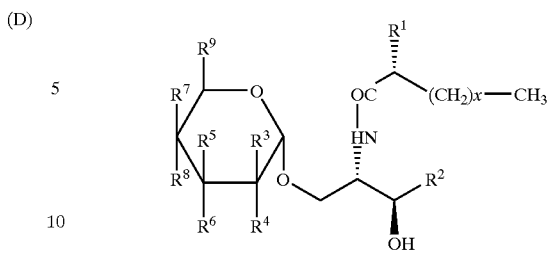
(I)

wherein $R^1$ represents H or OH,

X represents an integer between 7 and 27, $R^2$ represents a substituent selected from the group consisting of the following (a) to (e) (wherein Y represents an integer between 5 and 17):
  (a) —$CH_2(CH_2)_YCH_3$
  (b) —$CH(OH)(CH_2)_YCH_3$
  (c) —$CH(OH)(CH_2)_YCH(CH_3)_2$
  (d) —$CH=CH(CH_2)_Y(CH_3)$
  (e) —$CH(OH)(CH_2)_YCH(CH_3)CH_2CH_3$, and $R^3$ to $R^9$ represent substituents as defined in any one of the following i) and ii):
  i) when $R^3$, $R^6$ and $R^8$ represent H,
    $R^4$ represents H, OH, $NH_2$, $NHCOCH_3$, or a substituent selected from the group consisting of the following groups (A) to (D):

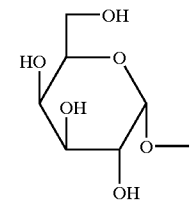
(A)

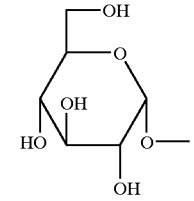
(B)

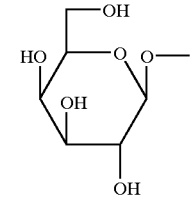
(C)

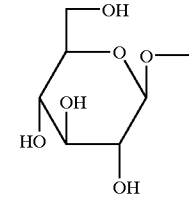
(D)

$R^5$ represents OH or a substituent selected from the group consisting of the following groups (E) and (F):

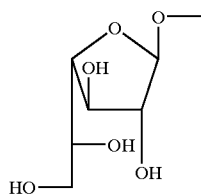
(E)

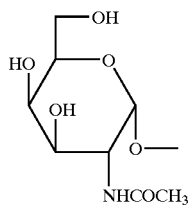
(F)

$R^7$ represents OH or a substituent selected from the group consisting of the following groups (A) to (D):

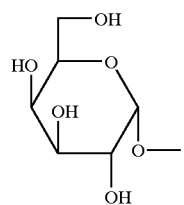
(A)

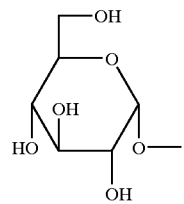
(B)

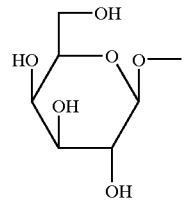
(C)

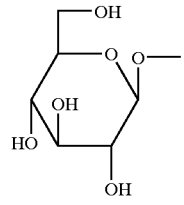
(D)

$R^9$ represents H, CH$_3$, CH$_2$OH or a substituent selected from the group consisting of the following groups (A') to (D'):

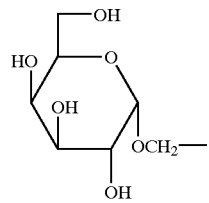
(A')

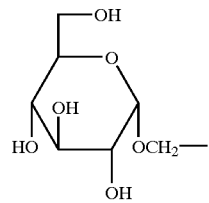
(B')

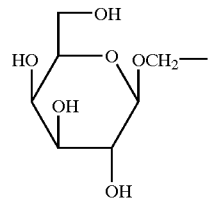
(C')

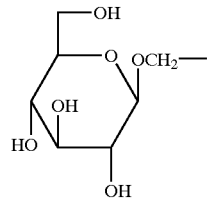
(D')

ii) when $R^3$, $R^6$ and $R^7$ represent H, $R^4$ represents H, OH, NH$_2$, NHCOCH$_3$, or substituent selected from the group consisting of the following groups (A) to (D):

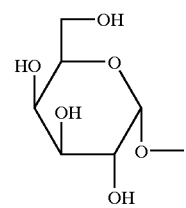
(A)

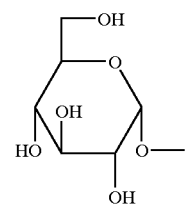
(B)

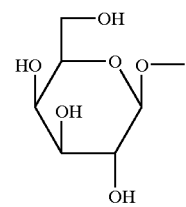
(C)

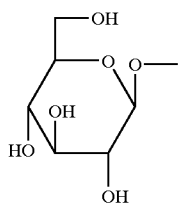 (D)

$R^5$ represents OH or a substituent selected from the group consisting of groups (E) and (F):

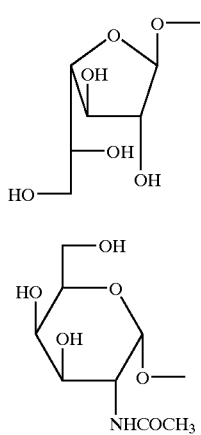
(E)

(F)

$R^8$ represents OH or a substituent selected from the group consisting of the following groups (A) to (D):

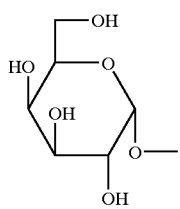 (A)

(B)

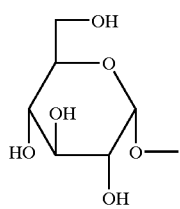 (C)

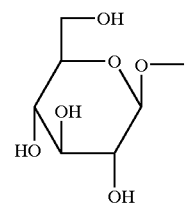 (D)

$R^9$ represents H, CH$_3$, CH$_2$OH or a substituent selected from the group consisting of the following groups (A') to (D'):

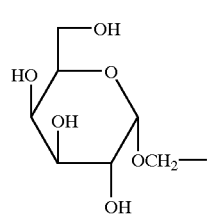
(A')

(B')

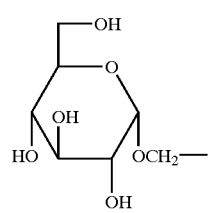
(C')

(D')

or a salt or solvate thereof.

7. The method of claim 6, further comprising inactivating the pathogen infected cell by radiation or a cytotoxic agent prior to administering.

* * * * *